(12) United States Patent
Barthe et al.

(10) Patent No.: US 9,700,340 B2
(45) Date of Patent: Jul. 11, 2017

(54) SYSTEM AND METHOD FOR ULTRA-HIGH FREQUENCY ULTRASOUND TREATMENT

(71) Applicant: Guided Therapy Systems LLC, Mesa, AZ (US)

(72) Inventors: Peter G. Barthe, Phoenix, AZ (US); Michael H. Slayton, Mesa, AZ (US)

(73) Assignee: Guided Therapy Systems, LLC, Mesa, AZ (US)

( * ) Notice: Subject to any disclaimer, the term of this patent is extended or adjusted under 35 U.S.C. 154(b) by 430 days.

(21) Appl. No.: 13/914,945

(22) Filed: Jun. 11, 2013

(65) Prior Publication Data

US 2013/0274603 A1    Oct. 17, 2013

Related U.S. Application Data

(63) Continuation of application No. 12/792,934, filed on Jun. 3, 2010, now Pat. No. 8,460,193, which is a
(Continued)

(51) Int. Cl.
*A61B 17/32* (2006.01)
*A61H 23/02* (2006.01)
(Continued)

(52) U.S. Cl.
CPC ........ *A61B 17/320068* (2013.01); *A61B 8/00* (2013.01); *A61H 23/0245* (2013.01); *A61N 7/02* (2013.01)

(58) Field of Classification Search
CPC ............. A61N 7/00; A61N 2007/0034; A61N 2007/0052; A61N 5/0616; A61B 2019/5276; A61B 8/00
(Continued)

(56) References Cited

U.S. PATENT DOCUMENTS

| 2,427,348 A | 9/1947 | Bond et al. |
| 3,913,386 A | 10/1975 | Saglio |

(Continued)

FOREIGN PATENT DOCUMENTS

| DE | 4029175 | 3/1992 |
| DE | 10140064 | 3/2003 |

(Continued)

OTHER PUBLICATIONS

Alster, Tinas S., Tanzi, Elizabeth L., "Cellulite Treatment using a Novel Combination Radiofrequency, Infrared Light, and Mechanical Tissue Manipulation Device," Journal of Cosmetic & Laser Therapy, Jun. 2005, vol. 7, Issue 2, pp. 81-85.

(Continued)

*Primary Examiner* — Peter Luong
(74) *Attorney, Agent, or Firm* — Quarles & Brady, LLP (57) ABSTRACT

A non-invasive ultra-high frequency ultrasound treatment method and system are provided. An exemplary method and system comprise a high-frequency ultrasound transducer system configured for providing ultrasound treatment to a patient such that the superficial and/or subcutaneous regions of the patient can be treated. An exemplary high-frequency ultrasound transducer system comprises a control system and a transducer configured to provide treatment to the superficial and/or subcutaneous regions of interest. The high-frequency ultrasound transducer may be configured to operate at higher frequencies and controlled power levels to provide treatment to the superficial and/or subcutaneous regions of interest. For example, higher frequencies within the range from approximately 20 MHz to 500 MHz or more may be utilized.

20 Claims, 3 Drawing Sheets

Related U.S. Application Data continuation of application No. 11/245,999, filed on Oct. 6, 2005, now Pat. No. 7,758,524.

(60) Provisional application No. 60/616,356, filed on Oct. 6, 2004.

(51) Int. Cl.
    *A61N 7/02* (2006.01)
    *A61B 8/00* (2006.01)

(58) Field of Classification Search
    USPC .................. 601/2–4; 600/407, 437, 439
    See application file for complete search history.

(56) References Cited

U.S. PATENT DOCUMENTS

| | | |
|---|---|---|
| 3,965,455 A | 6/1976 | Hurwitz |
| 3,992,925 A | 11/1976 | Perilhou |
| 4,039,312 A | 8/1977 | Patru |
| 4,059,098 A | 11/1977 | Murdock |
| 4,101,795 A | 7/1978 | Fukumoto |
| 4,166,967 A | 9/1979 | Benes et al. |
| 4,211,949 A | 7/1980 | Brisken et al. |
| 4,213,344 A | 7/1980 | Rose |
| 4,276,491 A | 6/1981 | Daniel |
| 4,315,514 A | 2/1982 | Drewes et al. |
| 4,325,381 A | 4/1982 | Glenn |
| 4,343,301 A | 8/1982 | Indech |
| 4,372,296 A | 2/1983 | Fahim |
| 4,379,145 A | 4/1983 | Masuho et al. |
| 4,381,007 A | 4/1983 | Doss |
| 4,381,787 A | 5/1983 | Hottinger |
| 4,397,314 A | 8/1983 | Vaguine |
| 4,409,839 A | 10/1983 | Taenzer |
| 4,431,008 A | 2/1984 | Wanner et al. |
| 4,441,486 A | 4/1984 | Pounds |
| 4,452,084 A | 6/1984 | Taenzer |
| 4,484,569 A | 11/1984 | Driller et al. |
| 4,507,582 A | 3/1985 | Glenn |
| 4,513,749 A | 4/1985 | Kino |
| 4,513,750 A | 4/1985 | Heyman et al. |
| 4,527,550 A | 7/1985 | Ruggera et al. |
| 4,528,979 A | 7/1985 | Marchenko |
| 4,534,221 A | 8/1985 | Fife et al. |
| 4,566,459 A | 1/1986 | Umemura et al. |
| 4,567,895 A | 2/1986 | Putzke |
| 4,586,512 A | 5/1986 | Do-Huu |
| 4,601,296 A | 7/1986 | Yerushalmi |
| 4,620,546 A | 11/1986 | Aida et al. |
| 4,637,256 A | 1/1987 | Sugiyama et al. |
| 4,646,756 A | 3/1987 | Watmough et al. |
| 4,663,358 A | 5/1987 | Hyon |
| 4,668,516 A | 5/1987 | Duraffourd et al. |
| 4,672,591 A | 6/1987 | Breimesser et al. |
| 4,680,499 A | 7/1987 | Umemura et al. |
| 4,697,588 A | 10/1987 | Reichenberger |
| 4,754,760 A | 7/1988 | Fukukita et al. |
| 4,757,820 A | 7/1988 | Itoh |
| 4,771,205 A | 9/1988 | Mequio |
| 4,801,459 A | 1/1989 | Liburdy |
| 4,803,625 A | 2/1989 | Fu et al. |
| 4,807,633 A | 2/1989 | Fry |
| 4,817,615 A | 4/1989 | Fukukita et al. |
| 4,858,613 A | 8/1989 | Fry et al. |
| 4,860,732 A | 8/1989 | Hasegawa et al. |
| 4,865,041 A | 9/1989 | Hassler |
| 4,865,042 A | 9/1989 | Umemura |
| 4,867,169 A | 9/1989 | Machida |
| 4,874,562 A | 10/1989 | Hyon |
| 4,875,487 A | 10/1989 | Seppi |
| 4,891,043 A | 1/1990 | Zeimer et al. |
| 4,893,624 A | 1/1990 | Lele |
| 4,896,673 A | 1/1990 | Rose |
| 4,900,540 A | 2/1990 | Ryan et al. |
| 4,901,729 A | 2/1990 | Saitoh et al. |
| 4,917,096 A | 4/1990 | Englehart |
| 4,973,096 A | 4/1990 | Jaworski |
| 4,932,414 A | 6/1990 | Coleman et al. |
| 4,938,216 A | 7/1990 | Lele |
| 4,938,217 A | 7/1990 | Lele |
| 4,947,046 A | 8/1990 | Kawabata et al. |
| 4,951,653 A | 8/1990 | Fry et al. |
| 4,955,365 A | 9/1990 | Fry et al. |
| 4,958,626 A | 9/1990 | Nambu |
| 4,976,709 A | 12/1990 | Sand |
| 4,979,501 A | 12/1990 | Valchanov |
| 4,992,989 A | 2/1991 | Watanabe et al. |
| 5,012,797 A | 5/1991 | Liang |
| 5,018,508 A | 5/1991 | Fry et al. |
| 5,030,874 A | 7/1991 | Saito et al. |
| 5,036,855 A | 8/1991 | Fry et al. |
| 5,040,537 A | 8/1991 | Katakura |
| 5,054,310 A | 10/1991 | Flynn |
| 5,054,470 A | 10/1991 | Fry et al. |
| 5,070,879 A | 12/1991 | Herres |
| 5,088,495 A | 2/1992 | Miyagawa |
| 5,115,814 A | 5/1992 | Griffith |
| 5,117,832 A | 6/1992 | Sanghvi et al. |
| 5,123,418 A | 6/1992 | Saurel |
| 5,143,063 A | 9/1992 | Fellner |
| 5,143,074 A | 9/1992 | Dory |
| 5,149,319 A | 9/1992 | Unger |
| 5,150,711 A | 9/1992 | Dory |
| 5,150,714 A | 9/1992 | Green |
| 5,152,294 A | 10/1992 | Mochizuki et al. |
| 5,156,144 A | 10/1992 | Iwasaki |
| 5,158,536 A | 10/1992 | Sekins |
| 5,159,931 A | 11/1992 | Pini |
| 5,163,421 A | 11/1992 | Bernstein |
| 5,163,436 A | 11/1992 | Saitoh et al. |
| 5,178,135 A | 1/1993 | Uchiyama et al. |
| 5,190,518 A | 3/1993 | Takasu |
| 5,190,766 A | 3/1993 | Ishihara |
| 5,191,880 A | 3/1993 | McLeod |
| 5,205,287 A | 4/1993 | Erbel et al. |
| 5,209,720 A | 5/1993 | Unger |
| 5,212,671 A | 5/1993 | Fujii et al. |
| 5,215,680 A | 6/1993 | D Arrigo |
| 5,224,467 A | 7/1993 | Oku |
| 5,230,334 A | 7/1993 | Klopotek |
| 5,230,338 A | 7/1993 | Allen et al. |
| 5,247,924 A | 9/1993 | Suzuki et al. |
| 5,255,681 A | 10/1993 | Ishimura et al. |
| 5,257,970 A | 11/1993 | Dougherty |
| 5,265,614 A | 11/1993 | Hayakawa |
| 5,267,985 A | 12/1993 | Shimada et al. |
| 5,269,297 A | 12/1993 | Weng |
| 5,282,797 A | 2/1994 | Chess |
| 5,295,484 A | 3/1994 | Marcus et al. |
| 5,295,486 A | 3/1994 | Wollschlaeger et al. |
| 5,304,169 A | 4/1994 | Sand |
| 5,305,756 A | 4/1994 | Entrekin et al. |
| 5,321,520 A | 6/1994 | Inga et al. |
| 5,323,779 A | 6/1994 | Hardy et al. |
| 5,327,895 A | 7/1994 | Hashimoto et al. |
| 5,348,016 A | 9/1994 | Unger et al. |
| 5,360,268 A | 11/1994 | Hayashi |
| 5,370,121 A | 12/1994 | Reichenberger et al. |
| 5,371,483 A | 12/1994 | Bhardwaj |
| 5,375,602 A | 12/1994 | Lancee et al. |
| 5,379,773 A | 1/1995 | Hornsby |
| 5,380,280 A | 1/1995 | Peterson |
| 5,380,519 A | 1/1995 | Schneider et al. |
| 5,383,917 A | 1/1995 | Desai et al. |
| 5,391,140 A | 2/1995 | Schaetzle et al. |
| 5,391,197 A | 2/1995 | Burdette et al. |
| 5,392,259 A | 2/1995 | Bolorforosh |
| 5,396,143 A | 3/1995 | Seyed-Bolorforosh et al. |
| 5,398,689 A | 3/1995 | Connor et al. |
| 5,406,503 A | 4/1995 | Williams, Jr. et al. |
| 5,417,216 A | 5/1995 | Tanaka |
| 5,419,327 A | 5/1995 | Rohwedder |
| 5,423,220 A | 6/1995 | Finsterwald et al. |

(56) References Cited

U.S. PATENT DOCUMENTS

| | | |
|---|---|---|
| 5,435,311 A | 7/1995 | Umemura et al. |
| 5,438,998 A | 8/1995 | Hanafy |
| 5,458,596 A | 10/1995 | Lax |
| 5,460,179 A | 10/1995 | Okunuki et al. |
| 5,460,595 A | 10/1995 | Hall et al. |
| 5,469,854 A | 11/1995 | Unger et al. |
| 5,471,988 A | 12/1995 | Fujio |
| 5,487,388 A | 1/1996 | Rello et al. |
| 5,492,126 A | 2/1996 | Hennige et al. |
| 5,496,256 A | 3/1996 | Bock |
| 5,501,655 A | 3/1996 | Rolt et al. |
| 5,503,152 A | 4/1996 | Oakley et al. |
| 5,503,320 A | 4/1996 | Webster et al. |
| 5,507,790 A | 4/1996 | Weiss |
| 5,520,188 A | 5/1996 | Hennige et al. |
| 5,522,869 A | 6/1996 | Burdette et al. |
| 5,523,058 A | 6/1996 | Umemura et al. |
| 5,524,620 A | 6/1996 | Rosenschein |
| 5,524,624 A | 6/1996 | Tepper |
| 5,524,625 A | 6/1996 | Okazaki et al. |
| 5,526,624 A | 6/1996 | Berg |
| 5,526,812 A | 6/1996 | Dumoulin et al. |
| 5,526,814 A | 6/1996 | Cline et al. |
| 5,526,815 A | 6/1996 | Granz et al. |
| 5,529,070 A | 6/1996 | Augustine et al. |
| 5,540,235 A | 7/1996 | Wilson |
| 5,558,092 A | 9/1996 | Unger et al. |
| 5,560,362 A | 10/1996 | Sliwa et al. |
| 5,575,291 A | 11/1996 | Hayakawa |
| 5,575,807 A | 11/1996 | Faller |
| 5,577,502 A | 11/1996 | Darrow et al. |
| 5,577,507 A | 11/1996 | Snyder et al. |
| 5,577,991 A | 11/1996 | Akui et al. |
| 5,580,575 A | 12/1996 | Unger et al. |
| 5,601,526 A | 2/1997 | Chapelon et al. |
| 5,603,323 A | 2/1997 | Pflugrath et al. |
| 5,609,562 A | 3/1997 | Kaali |
| 5,615,091 A | 3/1997 | Palatnik |
| 5,617,858 A | 4/1997 | Taverna et al. |
| 5,618,275 A | 4/1997 | Bock |
| 5,620,479 A | 4/1997 | Diederich |
| 5,622,175 A | 4/1997 | Sudol et al. |
| 5,638,819 A | 6/1997 | Manwaring et al. |
| 5,643,179 A | 7/1997 | Fujimoto |
| 5,644,085 A | 7/1997 | Lorraine et al. |
| 5,647,373 A | 7/1997 | Paltieli |
| 5,655,535 A | 8/1997 | Friemel et al. |
| 5,655,538 A | 8/1997 | Lorraine |
| 5,657,760 A | 8/1997 | Ying et al. |
| 5,658,328 A | 8/1997 | Johnson |
| 5,660,836 A | 8/1997 | Knowlton |
| 5,662,116 A | 9/1997 | Kondo et al. |
| 5,665,053 A | 9/1997 | Jacobs |
| 5,665,141 A | 9/1997 | Vago |
| 5,671,746 A | 9/1997 | Dreschel et al. |
| 5,673,699 A | 10/1997 | Trahey et al. |
| 5,676,692 A | 10/1997 | Sanghvi et al. |
| 5,685,820 A | 11/1997 | Riek et al. |
| 5,687,737 A | 11/1997 | Branham et al. |
| 5,690,608 A | 11/1997 | Watanabe |
| 5,694,936 A | 12/1997 | Fujimoto et al. |
| 5,697,897 A | 12/1997 | Buchholtz et al. |
| 5,701,900 A | 12/1997 | Shehada et al. |
| 5,704,361 A | 1/1998 | Seward et al. |
| 5,706,252 A | 1/1998 | Le Verrier et al. |
| 5,706,564 A | 1/1998 | Rhyne |
| 5,715,823 A | 2/1998 | Wood et al. |
| 5,720,287 A | 2/1998 | Chapelon et al. |
| 5,722,411 A | 3/1998 | Suzuki et al. |
| 5,727,554 A | 3/1998 | Kalend et al. |
| 5,735,280 A | 4/1998 | Sherman et al. |
| 5,743,863 A | 4/1998 | Chapelon |
| 5,746,005 A | 5/1998 | Steinberg |
| 5,746,762 A | 5/1998 | Bass |
| 5,748,767 A | 5/1998 | Raab |
| 5,749,364 A | 5/1998 | Sliwa et al. |
| 5,755,228 A | 5/1998 | Wilson et al. |
| 5,755,753 A | 5/1998 | Knowlton |
| 5,762,066 A | 6/1998 | Law et al. |
| 5,763,886 A | 6/1998 | Schulte |
| 5,769,790 A | 6/1998 | Watkins et al. |
| 5,779,644 A | 7/1998 | Eberle et al. |
| 5,792,058 A | 8/1998 | Lee et al. |
| 5,795,297 A | 8/1998 | Daigle |
| 5,795,311 A | 8/1998 | Wess |
| 5,810,009 A | 9/1998 | Mine et al. |
| 5,810,888 A | 9/1998 | Fenn |
| 5,814,599 A | 9/1998 | Mitragotri et al. |
| 5,817,013 A | 10/1998 | Ginn et al. |
| 5,817,021 A | 10/1998 | Reichenberger |
| 5,820,564 A | 10/1998 | Slayton |
| 5,823,962 A | 10/1998 | Schaetzle et al. |
| 5,827,204 A | 10/1998 | Grandia et al. |
| 5,840,032 A | 11/1998 | Hatfield et al. |
| 5,844,140 A | 12/1998 | Seale |
| 5,853,367 A | 12/1998 | Chalek et al. |
| 5,869,751 A | 2/1999 | Bonin |
| 5,871,524 A | 2/1999 | Knowlton |
| 5,873,902 A | 2/1999 | Sanghvi et al. |
| 5,876,431 A | 3/1999 | Spehr et al. |
| 5,879,303 A | 3/1999 | Averkiou et al. |
| 5,882,557 A | 3/1999 | Hayakawa |
| 5,891,034 A | 4/1999 | Bucholz |
| 5,899,861 A | 5/1999 | Friemel et al. |
| 5,904,659 A | 5/1999 | Duarte |
| 5,919,219 A | 7/1999 | Knowlton |
| 5,923,099 A | 7/1999 | Bilir |
| 5,924,989 A | 7/1999 | Polz |
| 5,928,169 A | 7/1999 | Schaetzle et al. |
| 5,931,805 A | 8/1999 | Brisken |
| 5,938,606 A | 8/1999 | Bonnefous |
| 5,938,612 A | 8/1999 | Kline-Schoder |
| 5,948,011 A | 9/1999 | Knowlton |
| 5,957,844 A | 9/1999 | Dekel |
| 5,957,882 A | 9/1999 | Nita et al. |
| 5,957,941 A | 9/1999 | Ream |
| 5,967,980 A | 10/1999 | Ferre et al. |
| 5,968,034 A | 10/1999 | Fulmer |
| 5,971,949 A | 10/1999 | Levin |
| 5,977,538 A | 11/1999 | Unger et al. |
| 5,984,882 A | 11/1999 | Rosenschein et al. |
| 5,990,598 A | 11/1999 | Sudol et al. |
| 5,997,471 A | 12/1999 | Gumb et al. |
| 5,997,497 A | 12/1999 | Nita et al. |
| 5,999,843 A | 12/1999 | Anbar |
| 6,004,262 A | 12/1999 | Putz et al. |
| 6,007,499 A | 12/1999 | Martin et al. |
| 6,013,032 A | 1/2000 | Savord |
| 6,016,255 A | 1/2000 | Bolan et al. |
| 6,019,724 A | 2/2000 | Gronningsaeter et al. |
| 6,022,308 A | 2/2000 | Williams |
| 6,022,327 A | 2/2000 | Chang |
| 6,036,646 A | 3/2000 | Barthe |
| 6,039,048 A | 3/2000 | Silberg |
| 6,039,689 A | 3/2000 | Lizzi |
| 6,042,556 A | 3/2000 | Beach et al. |
| 6,049,159 A | 4/2000 | Barthe |
| 6,050,943 A | 4/2000 | Slayton et al. |
| 6,059,727 A | 5/2000 | Fowlkes |
| 6,071,239 A | 6/2000 | Cribbs et al. |
| 6,080,108 A | 6/2000 | Dunham |
| 6,083,148 A | 7/2000 | Williams |
| 6,086,535 A | 7/2000 | Ishibashi et al. |
| 6,086,580 A | 7/2000 | Mordon et al. |
| 6,090,054 A | 7/2000 | Tagishi |
| 6,093,883 A | 7/2000 | Sanghvi |
| 6,101,407 A | 8/2000 | Groezinger |
| 6,106,469 A | 8/2000 | Suzuki et al. |
| 6,113,558 A | 9/2000 | Rosenschein et al. |
| 6,113,559 A | 9/2000 | Klopotek |
| 6,120,452 A | 9/2000 | Barthe |
| 6,123,081 A | 9/2000 | Durette |
| 6,126,619 A | 10/2000 | Peterson et al. |
| 6,135,971 A | 10/2000 | Hutchinson et al. |

(56) References Cited

U.S. PATENT DOCUMENTS

| | | |
|---|---|---|
| 6,139,499 A | 10/2000 | Wilk |
| 6,159,150 A | 12/2000 | Yale et al. |
| 6,171,244 B1 | 1/2001 | Finger et al. |
| 6,176,840 B1 | 1/2001 | Nishimura |
| 6,183,426 B1 | 2/2001 | Akisada |
| 6,183,502 B1 | 2/2001 | Takeuchi |
| 6,183,773 B1 | 2/2001 | Anderson |
| 6,190,323 B1 | 2/2001 | Dias |
| 6,190,336 B1 | 2/2001 | Duarte |
| 6,193,658 B1 | 2/2001 | Wendelken et al. |
| 6,210,327 B1 | 4/2001 | Brackett et al. |
| 6,213,948 B1 | 4/2001 | Barthe |
| 6,216,029 B1 | 4/2001 | Paltieli |
| 6,233,476 B1 | 5/2001 | Strommer et al. |
| 6,234,990 B1 | 5/2001 | Rowe et al. |
| 6,241,753 B1 | 6/2001 | Knowlton |
| 6,246,898 B1 | 6/2001 | Vesely et al. |
| 6,251,074 B1 | 6/2001 | Averkiou et al. |
| 6,251,088 B1 | 6/2001 | Kaufman et al. |
| 6,268,405 B1 | 7/2001 | Yao |
| 6,273,864 B1 | 8/2001 | Duarte |
| 6,280,402 B1 | 8/2001 | Ishibashi et al. |
| 6,287,257 B1 | 9/2001 | Matichuk |
| 6,296,619 B1 | 10/2001 | Brisken |
| 6,301,989 B1 | 10/2001 | Brown et al. |
| 6,309,355 B1 | 10/2001 | Cain et al. |
| 6,311,090 B1 | 10/2001 | Knowlton |
| 6,315,741 B1 | 11/2001 | Martin |
| 6,322,509 B1 | 11/2001 | Pan et al. |
| 6,322,532 B1 | 11/2001 | D'Sa |
| 6,325,540 B1 | 12/2001 | Lounsberry et al. |
| 6,325,758 B1 | 12/2001 | Carol et al. |
| 6,325,769 B1 | 12/2001 | Klopotek |
| 6,325,798 B1 | 12/2001 | Edwards et al. |
| 6,338,716 B1 | 1/2002 | Hossack et al. |
| 6,350,276 B1 | 2/2002 | Knowlton |
| 6,356,780 B1 | 3/2002 | Licato et al. |
| 6,361,531 B1 | 3/2002 | Hissong |
| 6,370,411 B1 | 4/2002 | Osadchy et al. |
| 6,375,672 B1 | 4/2002 | Aksan |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,390,982 B1 | 5/2002 | Bova et al. |
| 6,405,090 B1 | 6/2002 | Knowlton |
| 6,409,720 B1 | 6/2002 | Hissong |
| 6,413,216 B1 | 7/2002 | Cain et al. |
| 6,413,253 B1 | 7/2002 | Koop |
| 6,413,254 B1 | 7/2002 | Hissong |
| 6,419,648 B1 | 7/2002 | Vitek |
| 6,423,007 B2 | 7/2002 | Lizzi et al. |
| 6,425,865 B1 | 7/2002 | Salcudean |
| 6,425,867 B1 | 7/2002 | Vaezy et al. |
| 6,425,912 B1 | 7/2002 | Knowlton |
| 6,428,477 B1 | 8/2002 | Mason |
| 6,428,532 B1 | 8/2002 | Doukas |
| 6,430,446 B1 | 8/2002 | Knowlton |
| 6,432,057 B1 | 8/2002 | Mazess et al. |
| 6,432,067 B1 | 8/2002 | Martin |
| 6,432,101 B1 | 8/2002 | Weber |
| 6,436,061 B1 | 8/2002 | Costantino |
| 6,438,424 B1 | 8/2002 | Knowlton |
| 6,440,071 B1 | 8/2002 | Slayton |
| 6,440,121 B1 | 8/2002 | Weber |
| 6,443,914 B1 | 9/2002 | Costantino |
| 6,453,202 B1 | 9/2002 | Knowlton |
| 6,461,378 B1 | 10/2002 | Knowlton |
| 6,470,216 B1 | 10/2002 | Knowlton |
| 6,488,626 B1 | 12/2002 | Lizzi et al. |
| 6,491,657 B2 | 12/2002 | Rowe |
| 6,500,121 B1 | 12/2002 | Slayton |
| 6,500,141 B1 | 12/2002 | Irion |
| 6,508,774 B1 | 1/2003 | Acker et al. |
| 6,511,427 B1 | 1/2003 | Sliwa, Jr. et al. |
| 6,511,428 B1 | 1/2003 | Azuma |
| 6,514,244 B2 | 2/2003 | Pope |
| 6,517,484 B1 | 2/2003 | Wilk et al. |
| 6,524,250 B1 | 2/2003 | Weber |
| 6,540,679 B2 | 4/2003 | Slayton |
| 6,540,685 B1 | 4/2003 | Rhoads et al. |
| 6,540,700 B1 | 4/2003 | Fujimoto et al. |
| 6,554,771 B1 | 4/2003 | Buil et al. |
| 6,569,099 B1 | 5/2003 | Babaev |
| 6,569,108 B2 | 5/2003 | Sarvazyan et al. |
| 6,572,552 B2 | 6/2003 | Fukukita |
| 6,575,956 B1 | 6/2003 | Brisken et al. |
| 6,595,934 B1 | 7/2003 | Hissong |
| 6,599,256 B1 | 7/2003 | Acker |
| 6,607,498 B2 | 8/2003 | Eshel |
| 6,618,620 B1 | 9/2003 | Freundlich et al. |
| 6,623,430 B1 | 9/2003 | Slayton |
| 6,626,854 B2 | 9/2003 | Friedman |
| 6,626,855 B1 | 9/2003 | Weng et al. |
| 6,638,226 B2 | 10/2003 | He et al. |
| 6,645,162 B2 | 11/2003 | Friedman |
| 6,662,054 B2 | 12/2003 | Kreindel |
| 6,663,627 B2 | 12/2003 | Francischelli |
| 6,665,806 B1 | 12/2003 | Shimizu |
| 6,666,835 B2 | 12/2003 | Martin |
| 6,669,638 B1 | 12/2003 | Miller et al. |
| 6,685,640 B1 | 2/2004 | Fry |
| 6,692,450 B1 | 2/2004 | Coleman |
| 6,699,237 B2 | 3/2004 | Weber |
| 6,716,184 B2 | 4/2004 | Vaezy et al. |
| 6,719,449 B1 | 4/2004 | Laugharn, Jr. et al. |
| 6,719,694 B2 | 4/2004 | Weng et al. |
| 6,726,627 B1 | 4/2004 | Lizzi et al. |
| 6,733,449 B1 | 5/2004 | Krishnamurthy et al. |
| 6,749,624 B2 | 6/2004 | Knowlton |
| 6,773,409 B2 | 8/2004 | Truckai et al. |
| 6,775,404 B1 | 8/2004 | Pagoulatos et al. |
| 6,790,187 B2 | 9/2004 | Thompson et al. |
| 6,824,516 B2 | 11/2004 | Batten et al. |
| 6,835,940 B2 | 12/2004 | Morikawa et al. |
| 6,846,290 B2 | 1/2005 | Lizzi et al. |
| 6,875,176 B2 | 4/2005 | Mourad |
| 6,882,884 B1 | 4/2005 | Mosk et al. |
| 6,887,239 B2 | 5/2005 | Elstrom et al. |
| 6,889,089 B2 | 5/2005 | Behl |
| 6,896,657 B2 | 5/2005 | Willis |
| 6,902,536 B2 | 6/2005 | Manna et al. |
| 6,905,466 B2 | 6/2005 | Salgo |
| 6,918,907 B2 | 7/2005 | Kelly |
| 6,920,883 B2 | 7/2005 | Bessette |
| 6,921,371 B2 | 7/2005 | Wilson |
| 6,932,771 B2 | 8/2005 | Whitmore |
| 6,932,814 B2 | 8/2005 | Wood |
| 6,936,044 B2 | 8/2005 | McDaniel |
| 6,936,046 B2 | 8/2005 | Hissong |
| 6,945,937 B2 | 9/2005 | Culp et al. |
| 6,948,843 B2 | 9/2005 | Laugharn et al. |
| 6,953,941 B2 | 10/2005 | Nakano et al. |
| 6,958,043 B2 | 10/2005 | Hissong |
| 6,971,994 B1 | 12/2005 | Young et al. |
| 6,974,417 B2 | 12/2005 | Lockwood et al. |
| 6,976,492 B2 | 12/2005 | Ingle |
| 6,992,305 B2 | 1/2006 | Maezawa et al. |
| 6,997,923 B2 | 2/2006 | Anderson |
| 7,006,874 B2 | 2/2006 | Knowlton |
| 7,020,528 B2 | 3/2006 | Neev |
| 7,022,089 B2 | 4/2006 | Ooba |
| 7,058,440 B2 | 6/2006 | Heuscher et al. |
| 7,063,666 B2 | 6/2006 | Weng et al. |
| 7,070,565 B2 | 7/2006 | Vaezy et al. |
| 7,074,218 B2 | 7/2006 | Washington et al. |
| 7,094,252 B2 | 8/2006 | Koop |
| 7,108,663 B2 | 9/2006 | Talish et al. |
| 7,115,123 B2 | 10/2006 | Knowlton |
| 7,122,029 B2 | 10/2006 | Koop et al. |
| 7,142,905 B2 | 11/2006 | Slayton |
| 7,165,451 B1 | 1/2007 | Brooks et al. |
| 7,179,238 B2 | 2/2007 | Hissong |

(56) References Cited

U.S. PATENT DOCUMENTS

| | | |
|---|---|---|
| 7,189,230 B2 | 3/2007 | Knowlton |
| 7,229,411 B2 | 6/2007 | Slayton |
| 7,235,592 B2 | 6/2007 | Muratoglu |
| 7,258,674 B2 | 8/2007 | Cribbs |
| 7,273,459 B2 | 9/2007 | Desilets |
| 7,294,125 B2 | 11/2007 | Phalen et al. |
| 7,297,117 B2 | 11/2007 | Trucco et al. |
| 7,303,555 B2 | 12/2007 | Makin et al. |
| 7,327,071 B2 | 2/2008 | Nishiyama et al. |
| 7,331,951 B2 | 2/2008 | Eshel et al. |
| 7,332,985 B2 | 2/2008 | Larson, III et al. |
| 7,347,855 B2 | 3/2008 | Eshel |
| RE40,403 E | 6/2008 | Cho et al. |
| 7,393,325 B2 | 7/2008 | Barthe |
| 7,398,116 B2 | 7/2008 | Edwards |
| 7,399,279 B2 | 7/2008 | Abend et al. |
| 7,491,171 B2 | 2/2009 | Barthe et al. |
| 7,510,536 B2 | 3/2009 | Foley et al. |
| 7,530,356 B2 | 5/2009 | Slayton |
| 7,530,958 B2 | 5/2009 | Slayton |
| 7,571,336 B2 | 8/2009 | Barthe |
| 7,601,120 B2 | 10/2009 | Moilanen et al. |
| 7,615,015 B2 | 11/2009 | Coleman |
| 7,615,016 B2 | 11/2009 | Barthe |
| 7,686,763 B2 | 3/2010 | Vaezy et al. |
| 7,695,437 B2 | 4/2010 | Quistgaard et al. |
| 7,758,524 B2 | 7/2010 | Barthe |
| 7,789,841 B2 | 9/2010 | Huckle et al. |
| 7,824,348 B2 | 11/2010 | Barthe et al. |
| 7,846,096 B2 | 12/2010 | Mast et al. |
| 7,857,773 B2 | 12/2010 | Desilets et al. |
| 7,875,023 B2 | 1/2011 | Eshel et al. |
| 7,914,453 B2 | 3/2011 | Slayton et al. |
| 7,914,469 B2 | 3/2011 | Torbati |
| 7,931,611 B2 | 4/2011 | Novak et al. |
| 7,955,281 B2 | 6/2011 | Pedersen et al. |
| 7,967,764 B2 | 6/2011 | Lidgren et al. |
| 7,967,839 B2 | 6/2011 | Flock et al. |
| 8,057,389 B2 | 11/2011 | Barthe et al. |
| 8,057,465 B2 | 11/2011 | Sliwa, Jr. et al. |
| 8,066,641 B2 | 11/2011 | Barthe et al. |
| 8,123,707 B2 | 2/2012 | Huckle et al. |
| 8,128,618 B2 | 3/2012 | Gliklich et al. |
| 8,133,180 B2 | 3/2012 | Slayton et al. |
| 8,133,191 B2 | 3/2012 | Rosenberg et al. |
| 8,166,332 B2 | 4/2012 | Barthe et al. |
| 8,197,409 B2 | 6/2012 | Foley et al. |
| 8,206,299 B2 | 6/2012 | Foley et al. |
| 8,211,017 B2 | 7/2012 | Foley et al. |
| 8,262,591 B2 | 9/2012 | Pedersen et al. |
| 8,273,037 B2 | 9/2012 | Kreindel et al. |
| 8,282,554 B2 | 10/2012 | Makin et al. |
| 8,333,700 B1 | 12/2012 | Barthe et al. |
| 8,366,622 B2 | 2/2013 | Slayton et al. |
| 8,409,097 B2 | 4/2013 | Slayton et al. |
| 8,444,562 B2 | 5/2013 | Barthe et al. |
| 8,480,585 B2 | 7/2013 | Slayton et al. |
| 8,506,486 B2 | 8/2013 | Slayton et al. |
| 8,523,775 B2 | 9/2013 | Barthe et al. |
| 8,535,228 B2 | 9/2013 | Slayton et al. |
| 8,585,618 B2 | 11/2013 | Hunziker et al. |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,708,935 B2 | 4/2014 | Barthe et al. |
| 8,715,186 B2 | 5/2014 | Slayton et al. |
| 8,726,781 B2 | 5/2014 | Eckhoff et al. |
| 2001/0009997 A1 | 7/2001 | Pope |
| 2001/0009999 A1 | 7/2001 | Kaufman et al. |
| 2001/0014780 A1 | 8/2001 | Martin et al. |
| 2001/0014819 A1 | 8/2001 | Ingle et al. |
| 2001/0031922 A1 | 10/2001 | Weng et al. |
| 2001/0039380 A1 | 11/2001 | Larson et al. |
| 2001/0041880 A1 | 11/2001 | Brisken |
| 2002/0000763 A1 | 1/2002 | Jones |
| 2002/0002345 A1 | 1/2002 | Marlinghaus |
| 2002/0040199 A1 | 4/2002 | Klopotek |
| 2002/0040442 A1 | 4/2002 | Ishidera |
| 2002/0052550 A1 | 5/2002 | Madsen et al. |
| 2002/0055702 A1 | 5/2002 | Atala |
| 2002/0062077 A1 | 5/2002 | Emmenegger |
| 2002/0062142 A1 | 5/2002 | Knowlton |
| 2002/0072691 A1 | 6/2002 | Thompson et al. |
| 2002/0082528 A1 | 6/2002 | Friedman et al. |
| 2002/0082529 A1 | 6/2002 | Suorsa et al. |
| 2002/0082589 A1 | 6/2002 | Friedman et al. |
| 2002/0087080 A1 | 7/2002 | Slayton et al. |
| 2002/0095143 A1 | 7/2002 | Key |
| 2002/0099094 A1 | 7/2002 | Anderson |
| 2002/0115917 A1 | 8/2002 | Honda et al. |
| 2002/0128648 A1 | 9/2002 | Weber |
| 2002/0143252 A1 | 10/2002 | Dunne et al. |
| 2002/0156400 A1 | 10/2002 | Babaev |
| 2002/0161357 A1 | 10/2002 | Anderson |
| 2002/0165529 A1 | 11/2002 | Danek |
| 2002/0168049 A1 | 11/2002 | Schriever |
| 2002/0169394 A1 | 11/2002 | Eppstein et al. |
| 2002/0169442 A1 | 11/2002 | Neev |
| 2002/0173721 A1 | 11/2002 | Grunwald et al. |
| 2002/0193784 A1 | 12/2002 | Mchale et al. |
| 2002/0193831 A1 | 12/2002 | Smith |
| 2003/0009153 A1 | 1/2003 | Brisken et al. |
| 2003/0014039 A1 | 1/2003 | Barzell et al. |
| 2003/0018255 A1 | 1/2003 | Martin |
| 2003/0028111 A1 | 2/2003 | Vaezy et al. |
| 2003/0028113 A1 | 2/2003 | Gilbert et al. |
| 2003/0032900 A1 | 2/2003 | Ella |
| 2003/0036706 A1 | 2/2003 | Slayton |
| 2003/0040739 A1 | 2/2003 | Koop |
| 2003/0050678 A1 | 3/2003 | Sierra |
| 2003/0055417 A1 | 3/2003 | Truckai et al. |
| 2003/0060736 A1 | 3/2003 | Martin et al. |
| 2003/0065313 A1 | 4/2003 | Koop |
| 2003/0074023 A1 | 4/2003 | Kaplan |
| 2003/0083536 A1 | 5/2003 | Eshel |
| 2003/0092988 A1 | 5/2003 | Makin |
| 2003/0097071 A1 | 5/2003 | Halmann et al. |
| 2003/0099383 A1 | 5/2003 | Lefebvre |
| 2003/0125629 A1 | 7/2003 | Ustuner |
| 2003/0139790 A1 | 7/2003 | Ingle et al. |
| 2003/0171678 A1 | 9/2003 | Batten et al. |
| 2003/0171701 A1 | 9/2003 | Babaev |
| 2003/0176790 A1 | 9/2003 | Slayton |
| 2003/0191396 A1 | 10/2003 | Sanghvi |
| 2003/0200481 A1 | 10/2003 | Stanley |
| 2003/0212129 A1 | 11/2003 | Liu et al. |
| 2003/0212351 A1 | 11/2003 | Hissong |
| 2003/0212393 A1 | 11/2003 | Knowlton |
| 2003/0216795 A1 | 11/2003 | Harth |
| 2003/0220536 A1 | 11/2003 | Hissong |
| 2003/0220585 A1 | 11/2003 | Hissong |
| 2003/0229331 A1 | 12/2003 | Brisken et al. |
| 2003/0233085 A1 | 12/2003 | Giammarusti |
| 2003/0236487 A1 | 12/2003 | Knowlton |
| 2004/0000316 A1 | 1/2004 | Knowlton |
| 2004/0001809 A1 | 1/2004 | Brisken |
| 2004/0002705 A1 | 1/2004 | Knowlton |
| 2004/0010222 A1 | 1/2004 | Nunomura et al. |
| 2004/0015106 A1 | 1/2004 | Coleman |
| 2004/0030227 A1 | 2/2004 | Littrup |
| 2004/0039312 A1 | 2/2004 | Hillstead |
| 2004/0039418 A1 | 2/2004 | Elstrom |
| 2004/0041563 A1 | 3/2004 | Lewin et al. |
| 2004/0041880 A1 | 3/2004 | Ikeda et al. |
| 2004/0042168 A1 | 3/2004 | Yang et al. |
| 2004/0044375 A1 | 3/2004 | Diederich et al. |
| 2004/0049134 A1 | 3/2004 | Tosaya et al. |
| 2004/0049734 A1 | 3/2004 | Simske |
| 2004/0059266 A1 | 3/2004 | Fry |
| 2004/0068186 A1 | 4/2004 | Ishida et al. |

(56) References Cited

U.S. PATENT DOCUMENTS

| | | |
|---|---|---|
| 2004/0073079 A1 | 4/2004 | Altshuler et al. |
| 2004/0073113 A1 | 4/2004 | Salgo |
| 2004/0073115 A1 | 4/2004 | Horzewski et al. |
| 2004/0073116 A1 | 4/2004 | Smith |
| 2004/0073204 A1 | 4/2004 | Ryan et al. |
| 2004/0077977 A1 | 4/2004 | Ella et al. |
| 2004/0082857 A1 | 4/2004 | Schonenberger et al. |
| 2004/0082859 A1 | 4/2004 | Schaer |
| 2004/0102697 A1 | 5/2004 | Evron |
| 2004/0105559 A1 | 6/2004 | Aylward et al. |
| 2004/0122323 A1 | 6/2004 | Vortman et al. |
| 2004/0122493 A1 | 6/2004 | Ishbashi et al. |
| 2004/0143297 A1 | 7/2004 | Ramsey |
| 2004/0152982 A1 | 8/2004 | Hwang et al. |
| 2004/0158150 A1 | 8/2004 | Rabiner et al. |
| 2004/0186535 A1 | 9/2004 | Knowlton |
| 2004/0189155 A1 | 9/2004 | Funakubo |
| 2004/0206365 A1 | 10/2004 | Knowlton |
| 2004/0210214 A1 | 10/2004 | Knowlton |
| 2004/0217675 A1 | 11/2004 | Desilets |
| 2004/0249318 A1 | 12/2004 | Tanaka |
| 2004/0254620 A1 | 12/2004 | Lacoste et al. |
| 2004/0267252 A1 | 12/2004 | Washington |
| 2005/0033201 A1 | 2/2005 | Takahashi |
| 2005/0033316 A1 | 2/2005 | Kertz |
| 2005/0038340 A1 | 2/2005 | Vaezy et al. |
| 2005/0055073 A1 | 3/2005 | Weber |
| 2005/0061834 A1 | 3/2005 | Garcia et al. |
| 2005/0070961 A1 | 3/2005 | Maki et al. |
| 2005/0074407 A1 | 4/2005 | Smith |
| 2005/0080469 A1 | 4/2005 | Larson |
| 2005/0091770 A1 | 5/2005 | Mourad et al. |
| 2005/0096542 A1 | 5/2005 | Weng et al. |
| 2005/0104690 A1 | 5/2005 | Larson, III et al. |
| 2005/0113689 A1 | 5/2005 | Gritzky |
| 2005/0134314 A1 | 6/2005 | Prather et al. |
| 2005/0137656 A1 | 6/2005 | Malak |
| 2005/0143677 A1 | 6/2005 | Young et al. |
| 2005/0154313 A1 | 7/2005 | Desilets |
| 2005/0154314 A1 | 7/2005 | Quistgaard |
| 2005/0154332 A1 | 7/2005 | Zanelli |
| 2005/0154431 A1 | 7/2005 | Quistgaard |
| 2005/0187495 A1 | 8/2005 | Quistgaard |
| 2005/0191252 A1 | 9/2005 | Mitsui |
| 2005/0193451 A1 | 9/2005 | Quistgaard et al. |
| 2005/0197681 A1 | 9/2005 | Barolet et al. |
| 2005/0228281 A1 | 10/2005 | Nefos |
| 2005/0240170 A1 | 10/2005 | Zhang et al. |
| 2005/0251120 A1 | 11/2005 | Anderson et al. |
| 2005/0256406 A1 | 11/2005 | Barthe |
| 2005/0261584 A1 | 11/2005 | Eshel |
| 2005/0261585 A1 | 11/2005 | Makin et al. |
| 2005/0267454 A1 | 12/2005 | Hissong |
| 2005/0288748 A1 | 12/2005 | Li et al. |
| 2006/0004306 A1 | 1/2006 | Altshuler |
| 2006/0020260 A1 | 1/2006 | Dover et al. |
| 2006/0025756 A1 | 2/2006 | Francischelli |
| 2006/0042201 A1 | 3/2006 | Curry |
| 2006/0058664 A1 | 3/2006 | Barthe |
| 2006/0058671 A1 | 3/2006 | Vitek et al. |
| 2006/0058707 A1 | 3/2006 | Barthe |
| 2006/0058712 A1 | 3/2006 | Altshuler et al. |
| 2006/0074309 A1 | 4/2006 | Bonnefous |
| 2006/0074313 A1 | 4/2006 | Slayton |
| 2006/0074314 A1 | 4/2006 | Slayton |
| 2006/0074355 A1 | 4/2006 | Slayton |
| 2006/0079816 A1 | 4/2006 | Barthe |
| 2006/0079868 A1 | 4/2006 | Makin |
| 2006/0084891 A1 | 4/2006 | Barthe |
| 2006/0089632 A1 | 4/2006 | Barthe |
| 2006/0089688 A1 | 4/2006 | Panescu |
| 2006/0094988 A1 | 5/2006 | Tosaya et al. |
| 2006/0111744 A1 | 5/2006 | Makin |
| 2006/0116583 A1 | 6/2006 | Ogasawara et al. |
| 2006/0116671 A1 | 6/2006 | Slayton |
| 2006/0122508 A1 | 6/2006 | Slayton |
| 2006/0122509 A1 | 6/2006 | Desilets |
| 2006/0161062 A1 | 7/2006 | Arditi et al. |
| 2006/0184069 A1 | 8/2006 | Vaitekunas |
| 2006/0184071 A1 | 8/2006 | Klopotek |
| 2006/0189972 A1 | 8/2006 | Grossman |
| 2006/0206105 A1 | 9/2006 | Chopra |
| 2006/0229514 A1 | 10/2006 | Wiener |
| 2006/0241440 A1 | 10/2006 | Eshel |
| 2006/0241442 A1 | 10/2006 | Barthe |
| 2006/0241470 A1 | 10/2006 | Novak et al. |
| 2006/0250046 A1 | 11/2006 | Koizumi et al. |
| 2006/0282691 A1 | 12/2006 | Barthe |
| 2006/0291710 A1 | 12/2006 | Wang et al. |
| 2007/0032784 A1 | 2/2007 | Gliklich |
| 2007/0035201 A1 | 2/2007 | Desilets |
| 2007/0055154 A1 | 3/2007 | Torbati |
| 2007/0055155 A1 | 3/2007 | Owen et al. |
| 2007/0055156 A1 | 3/2007 | Desilets |
| 2007/0065420 A1 | 3/2007 | Johnson |
| 2007/0083120 A1 | 4/2007 | Cain et al. |
| 2007/0087060 A1 | 4/2007 | Dietrich |
| 2007/0088245 A1 | 4/2007 | Babaev et al. |
| 2007/0088346 A1 | 4/2007 | Mirizzi et al. |
| 2007/0161902 A1 | 7/2007 | Dan |
| 2007/0166357 A1 | 7/2007 | Shaffer et al. |
| 2007/0167709 A1 | 7/2007 | Slayton |
| 2007/0208253 A1 | 9/2007 | Slayton |
| 2007/0219604 A1 | 9/2007 | Yaroslavsky et al. |
| 2007/0219605 A1 | 9/2007 | Yaroslavsky et al. |
| 2007/0238994 A1 | 10/2007 | Stecco et al. |
| 2007/0239075 A1 | 10/2007 | Rosenberg et al. |
| 2007/0239079 A1 | 10/2007 | Manstein et al. |
| 2007/0239142 A1 | 10/2007 | Altshuler et al. |
| 2008/0027328 A1 | 1/2008 | Klopotek et al. |
| 2008/0039724 A1 | 2/2008 | Seip et al. |
| 2008/0071255 A1 | 3/2008 | Barthe |
| 2008/0086054 A1 | 4/2008 | Slayton |
| 2008/0097253 A1 | 4/2008 | Pederson |
| 2008/0139974 A1 | 6/2008 | Da Silva |
| 2008/0146970 A1 | 6/2008 | Litman et al. |
| 2008/0167556 A1 | 7/2008 | Thompson et al. |
| 2008/0183077 A1 | 7/2008 | Moreau-Gobard et al. |
| 2008/0188745 A1 | 8/2008 | Chen et al. |
| 2008/0195000 A1 | 8/2008 | Spooner et al. |
| 2008/0200810 A1 | 8/2008 | Buchalter |
| 2008/0200813 A1 | 8/2008 | Quistgaard |
| 2008/0214966 A1 | 9/2008 | Slayton |
| 2008/0221491 A1 | 9/2008 | Slayton |
| 2008/0223379 A1 | 9/2008 | Stuker et al. |
| 2008/0243035 A1 | 10/2008 | Crunkilton |
| 2008/0269608 A1 | 10/2008 | Anderson et al. |
| 2008/0275342 A1 | 11/2008 | Barthe |
| 2008/0281206 A1 | 11/2008 | Bartlett et al. |
| 2008/0281236 A1 | 11/2008 | Eshel et al. |
| 2008/0281237 A1 | 11/2008 | Slayton |
| 2008/0281255 A1 | 11/2008 | Slayton |
| 2008/0294073 A1 | 11/2008 | Barthe et al. |
| 2008/0319356 A1 | 12/2008 | Cain et al. |
| 2009/0005680 A1 | 1/2009 | Jones et al. |
| 2009/0012394 A1 | 1/2009 | Hobelsberger et al. |
| 2009/0043198 A1 | 2/2009 | Milner et al. |
| 2009/0043293 A1 | 2/2009 | Pankratov et al. |
| 2009/0069677 A1 | 3/2009 | Chen et al. |
| 2009/0093737 A1 | 4/2009 | Chomas et al. |
| 2009/0156969 A1 | 6/2009 | Santangelo |
| 2009/0171252 A1 | 7/2009 | Bockenstedt et al. |
| 2009/0177122 A1 | 7/2009 | Peterson |
| 2009/0177123 A1 | 7/2009 | Peterson |
| 2009/0182231 A1 | 7/2009 | Barthe et al. |
| 2009/0216159 A1 | 8/2009 | Slayton et al. |
| 2009/0226424 A1 | 9/2009 | Hsu |
| 2009/0227910 A1 | 9/2009 | Pedersen et al. |
| 2009/0253988 A1 | 10/2009 | Slayton et al. |
| 2009/0299175 A1 | 12/2009 | Bernstein et al. |
| 2009/0318909 A1 | 12/2009 | Debenedictis et al. |
| 2010/0011236 A1 | 1/2010 | Barthe et al. |
| 2010/0022919 A1 | 1/2010 | Peterson |
| 2010/0022922 A1 | 1/2010 | Barthe et al. |

(56) References Cited

U.S. PATENT DOCUMENTS

| | | |
|---|---|---|
| 2010/0042020 A1 | 2/2010 | Ben-Ezra |
| 2010/0049178 A1 | 2/2010 | Deem et al. |
| 2010/0063422 A1 | 3/2010 | Hynynen et al. |
| 2010/0130891 A1 | 5/2010 | Taggart et al. |
| 2010/0160782 A1 | 6/2010 | Slayton et al. |
| 2010/0160837 A1 | 6/2010 | Hunziker et al. |
| 2010/0168576 A1 | 7/2010 | Poland et al. |
| 2010/0191120 A1 | 7/2010 | Kraus et al. |
| 2010/0241035 A1 | 9/2010 | Barthe et al. |
| 2010/0280420 A1 | 11/2010 | Barthe et al. |
| 2010/0286518 A1 | 11/2010 | Lee et al. |
| 2011/0040171 A1 | 2/2011 | Foley et al. |
| 2011/0040190 A1 | 2/2011 | Jahnke et al. |
| 2011/0087099 A1 | 4/2011 | Eshel et al. |
| 2011/0087255 A1 | 4/2011 | Mccormack et al. |
| 2011/0112405 A1 | 5/2011 | Barthe et al. |
| 2011/0178444 A1 | 7/2011 | Slayton et al. |
| 2011/0190745 A1 | 8/2011 | Uebelhoer et al. |
| 2011/0264012 A1 | 10/2011 | Lautzenhiser et al. |
| 2012/0004549 A1 | 1/2012 | Barthe et al. |
| 2012/0016239 A1 | 1/2012 | Barthe et al. |
| 2012/0029353 A1 | 2/2012 | Slayton et al. |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |
| 2012/0111339 A1 | 5/2012 | Barthe et al. |
| 2012/0143056 A1 | 6/2012 | Slayton et al. |
| 2012/0165668 A1 | 6/2012 | Slayton et al. |
| 2012/0165848 A1 | 6/2012 | Slayton et al. |
| 2012/0197120 A1 | 8/2012 | Makin et al. |
| 2012/0197121 A1 | 8/2012 | Slayton et al. |
| 2012/0215105 A1 | 8/2012 | Slayton et al. |
| 2012/0271294 A1 | 10/2012 | Barthe et al. |
| 2012/0296240 A1 | 11/2012 | Azhari et al. |
| 2012/0316426 A1 | 12/2012 | Foley et al. |
| 2012/0330197 A1 | 12/2012 | Makin et al. |
| 2012/0330222 A1 | 12/2012 | Barthe et al. |
| 2012/0330223 A1 | 12/2012 | Makin et al. |
| 2013/0012755 A1 | 1/2013 | Slayton |
| 2013/0012816 A1 | 1/2013 | Slayton et al. |
| 2013/0012838 A1 | 1/2013 | Jaeger et al. |
| 2013/0012842 A1 | 1/2013 | Barthe |
| 2013/0018286 A1 | 1/2013 | Slayton et al. |
| 2013/0046209 A1 | 2/2013 | Slayton et al. |
| 2013/0066208 A1 | 3/2013 | Barthe et al. |
| 2013/0066237 A1 | 3/2013 | Smotrich et al. |
| 2013/0072826 A1 | 3/2013 | Slayton et al. |
| 2013/0096471 A1 | 4/2013 | Slayton et al. |
| 2013/0190659 A1 | 7/2013 | Slayton et al. |
| 2013/0211258 A1 | 8/2013 | Barthe et al. |
| 2013/0281853 A1 | 10/2013 | Slayton et al. |
| 2013/0281891 A1 | 10/2013 | Slayton et al. |
| 2013/0296697 A1 | 11/2013 | Slayton et al. |
| 2013/0296700 A1 | 11/2013 | Slayton et al. |
| 2013/0303904 A1 | 11/2013 | Barthe et al. |
| 2013/0303905 A1 | 11/2013 | Barthe et al. |
| 2013/0310863 A1 | 11/2013 | Barthe et al. |
| 2014/0082907 A1 | 3/2014 | Barthe |
| 2014/0142430 A1 | 5/2014 | Slayton et al. |
| 2014/0148834 A1 | 5/2014 | Barthe et al. |
| 2014/0180174 A1 | 6/2014 | Slayton et al. |
| 2014/0187944 A1 | 7/2014 | Slayton et al. |
| 2014/0188015 A1 | 7/2014 | Slayton et al. |
| 2014/0188145 A1 | 7/2014 | Slayton et al. |

FOREIGN PATENT DOCUMENTS

| | | | |
|---|---|---|---|
| DE | 10219217 | | 11/2003 |
| DE | 10219297 | | 11/2003 |
| DE | 20314479 | | 3/2004 |
| EP | 0344773 | | 12/1989 |
| EP | 1479412 | | 11/1991 |
| EP | 0473553 | A | 3/1992 |
| EP | 0661029 | A | 7/1995 |
| EP | 1050322 | | 11/2000 |
| EP | 1234566 | | 8/2002 |
| EP | 1262160 | | 12/2002 |
| EP | 1374944 | A | 1/2004 |
| GB | 2113099 | | 8/1983 |
| JP | 63036171 | | 2/1988 |
| JP | 03048299 | | 3/1991 |
| JP | 3123559 | | 5/1991 |
| JP | 03136642 | | 6/1991 |
| JP | 4089058 | | 3/1992 |
| JP | 04150847 | | 5/1992 |
| JP | 7080087 | | 3/1995 |
| JP | 07505793 | | 6/1995 |
| JP | 7222782 | | 8/1995 |
| JP | 09047458 | | 2/1997 |
| JP | 11505440 | | 5/1999 |
| JP | 11506636 | | 6/1999 |
| JP | 2000166940 | | 6/2000 |
| JP | 2001170068 | | 6/2001 |
| JP | 2002078764 | | 3/2002 |
| JP | 2002515786 | | 5/2002 |
| JP | 2002521118 | | 7/2002 |
| JP | 2002537939 | | 11/2002 |
| JP | 2003050298 | | 2/2003 |
| JP | 2003204982 | | 7/2003 |
| JP | 2004147719 | | 5/2004 |
| JP | 2005503388 | | 2/2005 |
| JP | 2005527336 | | 9/2005 |
| JP | 2005323213 | | 11/2005 |
| JP | 2006520247 | | 9/2006 |
| JP | 2007505793 | A | 3/2007 |
| JP | 2009518126 | | 5/2009 |
| JP | 2010517695 | | 5/2010 |
| KR | 1020010024871 | | 3/2001 |
| KR | 100400870 | B1 | 10/2003 |
| KR | 1020060113930 | | 11/2006 |
| KR | 1020070065332 | | 6/2007 |
| KR | 1020070070161 | | 7/2007 |
| KR | 1020070098856 | | 10/2007 |
| KR | 1020070104878 | | 10/2007 |
| KR | 1020070114105 | | 11/2007 |
| WO | 9625888 | | 8/1996 |
| WO | 9639079 | A1 | 12/1996 |
| WO | 9735518 | | 10/1997 |
| WO | 9832379 | | 7/1998 |
| WO | 9933520 | | 7/1999 |
| WO | 9949788 | | 10/1999 |
| WO | 0006032 | | 2/2000 |
| WO | 0015300 | | 3/2000 |
| WO | 0021612 | | 4/2000 |
| WO | 0053113 | | 9/2000 |
| WO | 0128623 | | 4/2001 |
| WO | 0182777 | | 11/2001 |
| WO | 0182778 | | 11/2001 |
| WO | 0187161 | | 11/2001 |
| WO | 0209813 | | 2/2002 |
| WO | 0224050 | | 3/2002 |
| WO | 02092168 | A | 11/2002 |
| WO | 02292168 | | 11/2002 |
| WO | 03053266 | A | 7/2003 |
| WO | 03065347 | | 8/2003 |
| WO | 03070105 | | 8/2003 |
| WO | 03077833 | | 8/2003 |
| WO | 03086215 | | 10/2003 |
| WO | 03096883 | | 11/2003 |
| WO | 03099177 | | 12/2003 |
| WO | 03101530 | | 12/2003 |
| WO | 04000116 | A | 12/2003 |
| WO | 2004080147 | | 9/2004 |
| WO | 2004110558 | | 12/2004 |
| WO | 2005011804 | A | 2/2005 |
| WO | 2005065408 | | 7/2005 |
| WO | 2005090978 | | 9/2005 |
| WO | 2006036870 | | 4/2006 |
| WO | 2006042163 | A | 4/2006 |
| WO | 2006042168 | | 4/2006 |
| WO | 2006042201 | | 4/2006 |
| WO | 2006065671 | | 6/2006 |
| WO | 2006082573 | | 8/2006 |

(56) References Cited

FOREIGN PATENT DOCUMENTS

| | | |
|---|---|---|
| WO | 2007067563 A | 6/2007 |
| WO | 2008024923 A2 | 2/2008 |
| WO | 2008036622 A | 3/2008 |
| WO | 2009013729 | 1/2009 |
| WO | 2009149390 A1 | 12/2009 |
| WO | 2014055708 A1 | 4/2014 |

OTHER PUBLICATIONS

Arthur et al., "Non-invasive estimation of hyperthermia temperatures with ultrasound," Int. J. Hyperthermia, Sep. 2005, 21(6), pp. 589-600.

Barthe et al., "Ultrasound therapy system and abiation results utilizing miniature imaging/therapy arrays," Ultrasonics Symposium, 2004 IEEE, Aug. 23, 2004, pp. 1792-1795, vol. 3.

Chen, L. et al., "Effect of Blood Perfusion on the ablation of liver perenchyma with high intensity focused ultrasount," Phys. Med. Biol; 38:1661-1673; 1993b.

Coon, Joshua et al., "Protein identification using sequential ion/ion reactions and tandem mass spectometry" Proceedings of the National Academy of Sciences of the USA, vol. 102, No. 27, Jul. 5, 2005, pp. 9463-9468.

Corry, Peter M., et al., "Human Cancer Treatment with Ultrasound", IEEE Transactions on Sonics and Ultrasonics, vol. SU-31, No. 5, Sep. 1984, pp. 444,456.

Damianou et al., Application of the Thermal Dose Concept for Predicting the Necrosed Tissue Volume During Ultrasound Surgery, 1993 IEEE Ultrasound Symposium, pp. 1199-1202.

Daum et al., "Design and Evaluation of a Feedback Based Phased Array System for Ultrasound Surgery," IEEE Transactions on Ultrasonics, Feroelectronics, and Frequency Control, vol. 45, No. 2, Mar. 1998, pp. 431-438.

Davis, Brian J., et al., "An Acoustic Phase Shift Technique for the Non-Invasive Measurement of Temperature Changes in Tissues", 1985 Ultrasonics Symposium, pp. 921-924.

Fry, W.J. et al., "Production of Focal Destructive Lesions in the Central Nervous System with Ultrasound," J. Neurosurg., 11:471-478; 1954.

Gliklich et al., Clinical Pilot Study of Intense Ultrasound therapy to Deep Dermal Facial Skin and Subcutaneous Tissues, Arch Facial Plastic Surgery, Mar. 1, 2007, vol. 9.

Harr, G.R. et al., "Tissue Destruction with Focused Ultrasound in Vivo," Eur. Urol. 23 (suppl. 1):8-11; 1993.

Hassan et al., "Structure and Applications of Poly(vinyl alcohol) Hydrogels Produced by Conventional Crosslinking or by Freezing/Thawing Methods," advanced in Polymer Science, 2000, pp. 37-65, vol. 153.

Hassan et al., "Structure and Morphology of Freeze/Thawed PVA Hydrogels," Macromolecules, Mar. 11, 2000, pp. 2472-2479, vol. 33, No. 7.

Husseini et al, "The Role of Cavitation in Acoustically Activated Drug Delivery," J. Control Release, Oct. 3, 2005, pp. 253-261, vol. 107(2).

Husseini et al. "Investigating the mechanism of accoustically activated uptake of drugs from Pluronic micelles," BMD Cancer 2002, 2:20k, Aug. 30, 2002, pp. 1-6.

Jeffers et al., "Evaluation of the Effect of Cavitation Activity on Drug-Ultrasound Synergisms," 1993 IEEE Ultrasonics Symposium, pp. 925-928.

Jenne, J., et al., "Temperature Mapping for High Energy US-Therapy", 1994 Ultrasonics Symposium, pp. 1879-1882.

Johnson, S.A., et al., "Non-Intrusive Measurement of Microwave and Ultrasound-Induced Hyperthermia by Acoustic temperature Tomography", Ultrasonics Symposium Proceedings, pp. 977-982.

Madersbacher, S. et al., "Tissue Ablation in Bening Prostatic Hyperplasia with High Intensity Focused Ultrasound," Dur. Urol., 23 (suppl. 1):39-43; 1993.

Makin et al, "B-Scan Imaging and Thermal Lesion Monitoring Using Miniaturized Dual-Functionality Ultrasound Arrays," Ultrasonics Symposium, 2004 IEEE, Aug. 23, 2004, pp. 1788-1791, vol. 3.

Makin et al, "Miniaturized Ultrasound Arrays for Interstitial Ablation and Imaging," UltraSound Med. Biol. 2005, Nov. 1, 2005, pp. 1539-1550, vol. 31(11).

Makin et al., "Confirmal Bulk Ablation and Therapy Monitoring Using Intracorporeal Image-Treat Ultrasound Arrays", 4th International Symposium on Therapeutic Ultrasound, Sep. 19, 2004.

Manohar et al, "Photoaccoustic mammography laboratory prototype: imaging of breast tissue phantoms," Journal of Biomedical Optics, Nov./Dec. 2004, pp. 1172-1181, vol. 9, No. 6.

Mast et al, "Bulk Ablation of Soft Tissue with Intense Ultrasound; Modeling nad Experiments," J. Acoust. Soc. Am., Oct. 1, 2005, pp. 2715-2724, vol. 118(4).

Mitragotri, Samir; "Healing sound: the use of ultrasound in drug delivery and other therapeutic applications," Nature Reviews; Drug Delivery, pp. 255-260, vol. 4.

Paradossi et al., "Poly(vinyl alcohol) as versatile biomaterial for potential biomedical applications," Journal of Materials Science: Materials in Medicine, 2003, pp. 687-691, vol. 14.

PCT/US2012/046122 International Search Report Jan. 30, 2013.

PCT/US2012/046123 International Search Report Jan. 28, 2013.

PCT/US2012/046125 International Search Report Jan. 28, 2013.

Reid, Gavin, et al., "Tandem Mass spectrometry of ribonuclease A and B: N-linked glycosylation site analysis of whole protein ions," Analytical Chemistry. Feb. 1, 2002, vol. 74, No. 3, pp. 577-583.

Righetti et al, "Elastographic Characterization of HIFU-Induced Lesions in Canine Livers," 1999, Ultrasound in Med & Bio, vol. 25, No. 7, pp. 1099-1113.

Saad et al., "Ultrasound-Enhanced Effects of Adriamycin Against Murine Tumors," Ultrasound in Med. & Biol. vol. 18, No. 8, pp. 715-723 (1992).

Sanghvi, N.T., et al., "Transrectal Ablation of Prostate Tissue Using Focused Ultrasound," 1993 Ultrasonics Symposium, IEEE, pp. 1207-1210.

Sassen, Sander, "ATI's R520 architecture, the new king of the hill?" http://www.hardwareanalysis.com/content/article/1813, Sep. 16, 2005, 2 pages.

Seip, Ralf, et al., "Noninvasive Detection of Thermal Effects Due to Highly Focused Ultrasonic Fiels," IEEE Symposium, pp. 1229-1232, vol. 2, Oct. 3-Nov. 1993.

Seip, Ralf, et al., "Noninvasive Estimation of Tissue Temperature Response to Heating Fields Using Diagnostic Ultrasound," IEEE Transactions on Biomedical Engineering, vol. 42, No. 8, Aug. 1995, pp. 828-839.

Simon et al., "Applications of Lipid-Coated Microbubble Ultrasonic Contrast to Tumor Therapy," Ultrasound in Med. & Biol. vol. 19, No. 2, pp. 123-125 (1993).

Smith, Nadine Barrie, et al., "Non-Invasive In Vivo Temperature Mapping of Ultrasound Heating Using Magnetic Resonance Techniques", 1994 Ultrasonics Symposium, pp. 1829-1832, vol. 3.

Surry et al., "Poly(vinyl alcohol) cryogel phantoms for use in ultrasound and MR imaging," Phys. Med. Biol., Dec. 6, 2004, pp. 5529-5546, vol. 49.

Syka J. E. P. et al., "Peptide and Protein Sequence Analysis by Electron Transfer Dissociation Mass Spectometry," Proceedings of the National Academy of Sciences of USA, National Academy of Aceince, Washington, DC, vol. 101, No. 26, Jun. 29, 2004, pp. 9528-9533.

Talbert, D. G., "An Add-On Modification for Linear Array Real-Time Ultrasound Scanners to Produce 3D Displays," UTS Int'l 1977 Brighton, England (Jun. 28-30, 1977) pp. 57-67.

Tata et al., "Interaction of Ultrasound and Model Membrane Systems: Analyses and Predictions," American Chemical Society, Phys. Chem. 1992, 96, pp. 3548-3555.

Ueno, S., et al., "Ultrasound Thermometry in Hyperthermia", 1990 Ultrasonic Symposium, pp. 1645-1652.

Wang, H., et al., "Limits on Focused Ultrasound for Deep Hyperthermia", 1994 Ultrasonic Symposium, Nov. 1-4, 1994, pp. 1869-1872, vol. 3.

Wasson, Scott, "NVIDIA's GeFroce 7800 GTX graphics processor Power MADD," http://techreport.com/reviews/2005q2/geforce-7800gtx/index.x?pg=1, Jun. 22, 2005, 4 pages.

(56) References Cited

OTHER PUBLICATIONS

White et al "Selective Creation of Thermal Injury Zones in the Superficial Musculoaponeurotic System Using Intense Ultrasound Therapy," Arch Facial Plastic Surgery, Jan./Feb. 2007, vol. 9, No. 1.
PCT International Search Report and Written Opinion, PCT/US2014/030779, Sep. 1, 2014, 8 pages.
European Patent Office, Examination Report, EP 07814933.3, Aug. 5, 2014, 5 pages.
European Patent Office, Examination Report, EP 05798870.1, Oct. 20, 2014, 5 pages.
European Patent Office, Examination Report, EP 10185100.4, Oct. 24, 2014, 4 pages.
European Patent Office, Examination Report, EP 10185112.9, Oct. 24, 2014, 5 pages.
European Patent Office, Examination Report, EP 10185117.8, Oct. 24, 2014, 5 pages.
European Patent Office, Examination Report, EP 10185120.2, Oct. 24, 2014, 4 pages.
European Examination Report in related Application No. 05808908.7 dated Jun. 29, 2009.
European Examination Report in related Application No. 05810308.6 dated Jun. 29, 2009.
European Examination Report in related Application No. 10185100.4 dated Jan. 6, 2014.
European Examination Report in related Application No. 10185120.2 dated Jan. 22, 2014.
Decision of the Korean Intellectual Property Tribunal dated Jun. 28, 2013 regarding Korean Patent No. 10-1142108, which is related to the pending appliction and/or an application identified in the Table on the pp. 2-5 of the information Disclosure Statement herein (English translation, English translation certification, and Korean decision included).
International Search Report and Written Opinion dated Jan. 23, 2014 in Application No. PCT/US2012/046122.
International Search Report and Written Opinion dated Jan. 23, 2014 in Application No. PCT/US2012/046123.
International Search Report and Written Opinion dated Jan. 28, 2012 in Application No. PCT/US2012/046327.
International Search Report and Written Opinion dated Jan. 28, 2013 in Application No. PCT/US2012/046125.
International Search Report and Written Opinion dated Feb. 14, 2013 in Application No. PCT/US2011/001361.
International Search Report and Written Opinion dated Feb. 14, 2013 in Application No. PCT/US2011/001362.
International Search Report and Written Opinion dated Feb. 14, 2013 in Application No. PCT/US2011/001366.
International Search Report and Written Opinion dated Apr. 6, 2012 in Application No. PCT/US2011/001367.
Calderhead et al., One Mechanism Behind LED Photo-Therapy for Wound Healing and Skin Rejuvenation: Key of the Mast Cell, Laser Therapy, Jul. 2008, pp. 141-148, 17.3.
European Examination Report in related Application No. 09835856.7 dated Apr. 11, 2004.
International Search Report and Written Opinion dated Apr. 6, 2012 in Application No. PCT/US2011/001366.

SYSTEM AND METHOD FOR ULTRA-HIGH FREQUENCY ULTRASOUND TREATMENT

CROSS-REFERENCE TO RELATED APPLICATIONS

This Application is a continuation of U.S. application Ser. No. 12/792,934 entitled "SYSTEM AND METHOD FOR ULTRA-HIGH FREQUENCY ULTRASOUND TREATMENT" which was filed on Jun. 3, 2010, now U.S. Pat. No. 8,460,193, which is a continuation of U.S. application Ser. No. 11/245,999 entitled "SYSTEM AND METHOD FOR ULTRA-HIGH FREQUENCY ULTRASOUND TREATMENT" which was filed on Oct. 6, 2005, now U.S. Pat. No. 7,758,524, issued Jul. 20, 2010 which in turn claims priority to and benefit of U.S. Provisional Application No. 60/616, 356, entitled "System and Method for Ultra-High frequency", and filed on Oct. 6, 2004, all of which are incorporated herein by reference.

FIELD OF INVENTION

This invention generally relates to an ultrasound system, and more particularly, to a method and system for ultra-high frequency ultrasound treatment.

BACKGROUND OF THE INVENTION

Many conventional applications of therapeutic ultrasound have employed low frequency transducers. These transducers have operational frequencies that typically range from 500 kHz to 1.5 MHz. Such low frequency transducers are often preferred because they allow for acoustical energy to be focused very deep into the body, without harming the overlying tissue structures.

Figure 1:
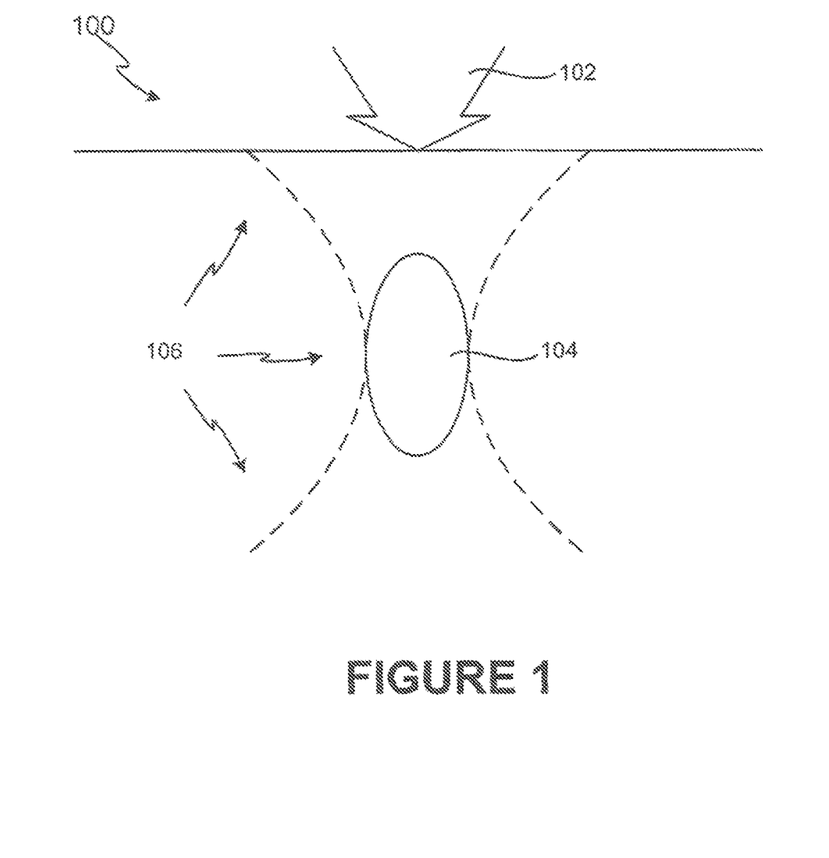
FIG. 1 illustrates a diagram of treatment application using a prior art low-frequency ultrasound treatment system.

A conventional application of non-invasive therapeutic ultrasound using a low frequency transducer is depicted in FIG. 1. A conventional low-frequency therapeutic application 100 utilizes low frequency energy 102 to treat a deep treatment region 104, such as a deep-seated lesion. Deep treatment region 104 is located at a depth well below a superficial region of a patient. Use of the low-frequency transducer generates an isonified tissue region 106 that can range from 2 cm to 10 cm below the skin surface. Unfortunately, currently available low frequency transducers cannot be used to treat the superficial regions, thus limiting the use of low-frequency application 100. For example, most cosmetic surgeries, as well as treatment of melanomas and skin disorders, require treatment to superficial regions, thus eliminating the use of lower frequency transducers.

Another undesirable side effect of low-frequency therapy is that the acoustic energy must pass through intervening tissue layers before reaching the desired deep treatment area. The intervening layers tend to defocus the rays and absorb some of the acoustic energy. This causes the focal spot size to widen, making it difficult to control the location of the focal spot, and making dosimetry also difficult to optimize.

SUMMARY OF THE INVENTION

In accordance with various aspects of the present invention, a non-invasive ultra-high frequency ultrasound treatment method and system are provided. An exemplary method and system comprise an ultra-high frequency ultrasound transducer system configured for providing ultrasound treatment to a patient such that the superficial regions of the patient can be treated extracorporeally and internal tissues can be treated superficially in a minimally invasive fashion.

An exemplary ultra-high frequency ultrasound transducer system comprises a control system and a transducer configured to provide treatment to the superficial and/or internal superficial regions of interest. The ultra-high frequency ultrasound transducer may be configured to operate at higher frequencies and controlled power levels to provide safe, controlled treatment to superficial, and/or internal superficial tissue, e.g. an organ or tissue surface regions of interest. For example, higher frequencies within the range from approximately 20 MHz to 500 MHz or more may be utilized. In addition, by operating at optimum efficiency, the acoustic intensity can be suitably configured at high levels with the use of controlled, moderate power output levels. In accordance with an exemplary embodiment of the present invention, the ultra-high frequency ultrasound transducer can comprise a transduction element having a piezoelectrically active layer, matching layers and/or other materials for generating radiation or acoustical energy. The transduction element can comprise single or multiple elements.

In accordance with an exemplary embodiment of the present invention, the transduction element may be configured with an application device to facilitate coupling of the acoustical energy to the superficial and/or internal superficial regions of interest. The application device may be configured in various manners for coupling to the patient to provide treatment to the superficial and/or internal superficial regions of interest. In accordance with another exemplary embodiment, the transduction element may be configured on a minimally-invasive application device, such as a needle or other medical instrument, to permit the transduction element to come into substantially direct contact with various facia, e.g., the SMAS tissue layers, to facilitate treatment. Thus, instead of being placed on the outer surface of the skin, the application device may be inserted into the patient to come into more proximate acoustical contact with the targeted region for treatment.

In accordance with an exemplary embodiment of the present invention, an exemplary control system comprises a drive circuit and a feedback network configured to control the operation of the ultra-high frequency ultrasound transducer. The drive circuit is configured to control power to the transduction element and can comprise various configurations, with and without voltage oscillation. In accordance with in exemplary embodiment, the drive circuit is configured to drive the frequency of the transduction element at the resonant frequency to facilitate maximum efficiency and/or maximum acoustic output. The feedback element is configured to use electrical signals from the driver circuit and/or the transduction element to facilitate control of the frequency of operation to provide optimum electro-acoustic conversion of energy. In addition, the control system can he suitably coupled to the transduction element in various manners.

In accordance with another aspect of the present invention, an ultra-high frequency ultrasound transducer system configured for providing ultrasound treatment to various depth regions within the superficial and/or internal superficial regions of the patient through control of the frequency of the transduction element and/or the cooling of the exemplary applicator device is provided.

BRIEF DESCRIPTION OF THE DRAWINGS

The subject matter of the invention is particularly pointed out and distinctly claimed in the concluding portion of the specification. The invention, however, both as to organization and method of operation, may best be understood by reference to the following description taken in conjunction with the claims and the accompanying drawing figures, in which like parts may be referred to by like numerals:

DETAILED DESCRIPTION

The present invention may be described herein in terms of various components and processing steps. It should he appreciated that such components and steps may be realized by any number of hardware devices and components configured to perform the specified functions. For example, the present invention may employ various medical treatment devices, visual imaging and display devices, input terminals and the like, which may carry out a variety of functions under the control of one or more control systems or other control devices. In addition, the present invention may be practiced in any number of medical or treatment contexts and that the exemplary embodiments relating to ultra-high frequency ultrasound treatment as described herein are merely a few of the exemplary applications for the invention. Far example, the principles, features and methods discussed may be applied to any medical or other tissue or treatment application.

In accordance with various aspects of the present invention, a non-invasive ultra-high frequency ultrasound treatment method and system are provided. An exemplary method and system comprise an ultra-high frequency ultrasound transducer system configured for providing ultrasound treatment to a patient such that superficial and/or internal superficial regions of a patient can be treated.

Figure 2:
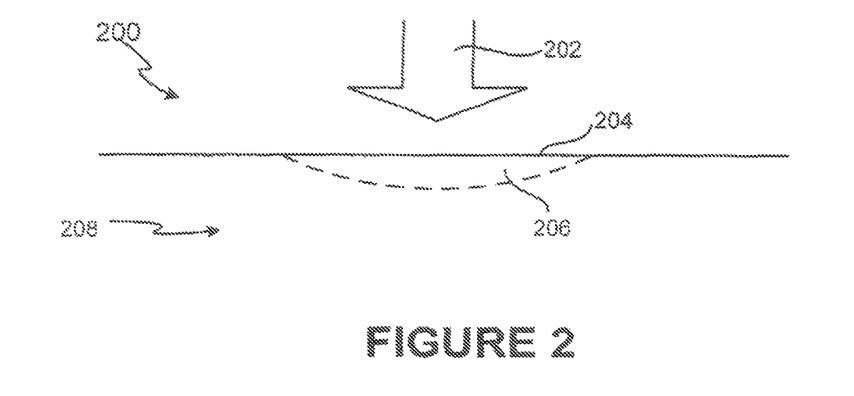
FIG. 2 illustrates a diagram of an ultra-high frequency ultrasound treatment application in accordance with an exemplary embodiment of the present invention.

With reference to FIG. 2, an exemplary ultra-high frequency ultrasound application 200 can comprise the applying of ultra-high frequency acoustical energy 202 to a superficial region 204 and/or internal superficial region 206 of a patient. Superficial region 204 comprises the skin layer of a patient e.g., the outermost epidermis layer that can comprise between approximately 0.1 µm to 100 µm and the inner dermis layer between approximately 0.1 mm and 3 mm or more. The internal superficial region comprises the superficial layers of internal organs or tissue, for example between approximately 0 mm to 3 mm or more. Ultra-high frequency acoustical energy 202 is configured for operating at higher frequencies and suitable power levels such that the frequency dependent acoustic absorption provides treatment only at the superficial region 204 or internal superficial region.

For example, higher frequencies within the range from approximately 20 MHz to 500 MHz or more may be utilized to cause absorption within the regions of interest, such as within the epidermis layers and/or just below the dermis skin layers of the patient. Moreover, acoustic power levels may be configured to optimise the frequency dependent acoustic absorption at the ultra-high frequency levels to facilitate treatment to the regions of interest. By operating at optimum efficiency, the acoustic intensity can be suitably configured at high levels with the use of controlled, moderate power output levels. For example, for a steady-state ultrasound intensity of approximately 500 W/cm$^2$ at the outermost epidermis layer, the acoustical intensity can be configured to drop one to two orders of magnitude using the ultra-high frequencies, thus becoming highly absorbed as the energy penetrates the skin layers, e.g., at 300 MHz, the acoustical intensity drops to approximately 15 W/cm$^2$ at a depth of approximately 100 µm. As a result, the acoustic intensity is configured to be relatively large at the region of interest between superficial region 204 and treatment region 206, and then rapidly drop off to lower levels proximate to region 208. Accordingly, ultra-high frequency acoustical energy 202 can be used to suitably ablate superficial region 204, as well as internal superficial tissue and/or treat treatment region 206 while leaving region 208 unaffected.

An exemplary high-frequency ultrasound transducer system can provide ultra-high frequency acoustical energy 202 in various configurations. For example, its accordance with an exemplary embodiment, with reference to FIG. 3, exemplary ultra-high frequency ultrasound system 300 comprises a control system 302 and a transducer 304 configured to provide treatment to a region of interest 306 within the superficial and/or internal superficial regions of a patient. In providing treatment, ultra-high frequency ultrasound system 300 may provide therapy, imaging and/or temperature monitoring to region of interest 306.

Figure 3:
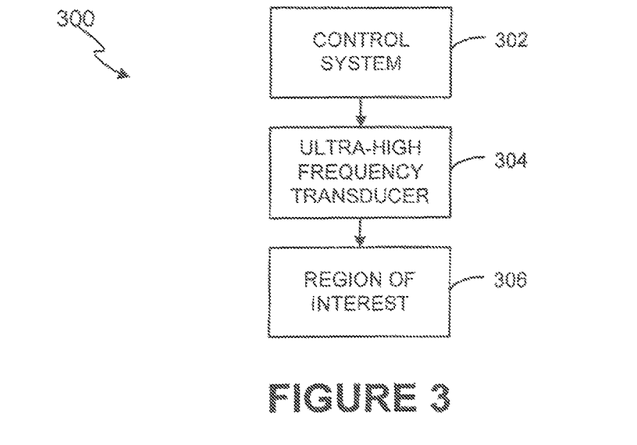
FIG. 3 illustrates a block diagram of an ultra-high frequency ultrasound treatment system in accordance with an exemplary embodiment of the present invention.

Control system 302 is configured for control and operation of transducer 304 to provide treatment. Control system 302 may comprise a processor, a display, and/or one or more input devices. In accordance with, an exemplary embodiment, as discussed in more detail below, control system 302 can also comprise an electronic drive and control unit including a drive circuit, power supply and other electronic control devices that can be configured to drive the frequency of transducer 304 in a controlled manner for maximum efficiency. The processor may comprise a personal computer, a Unix system, or any other conventional processing unit. The display may comprise a monitor, LCD screen, or any other device configured to display an image. An input/output device may comprise a keyboard, a mouse, a touchscreen, or any other device for transmitting or receiving information to and from a control system. An "on/off" pushbutton or other control inputs may also be configured within control system 302. The information from the input device and images displayed may be received or transmitted in any format, such as manually, by analog device, by digital device, and/or by any other mechanisms.

The processor, display, electronic drive and control devices and/or input devices may be coupled together in any manner. By coupling, the devices comprising control system 304 may be directly connected to each other or may be connected through one or more other devices or components that allow a signal to travel to/from one component to another. The various coupling components for the devices comprising control system 304 can include but are not limited to the internet, a wireless network, a conventional wire cable, an optical cable or connection through air, water, or any other medium, that conducts signals, and any other coupling device or medium.

Transducer 304 is configured to operate at ultra-high frequencies. For example, frequencies within the range from approximately 20 MHz to 400 MHz or more may be selected to cause acoustic absorption within region of interest 306, i.e., within the outer epidermis layers, and/or just below the skin layers of the patient through the subcutaneous fat region. In accordance with an exemplary embodiment, transducer 304 can also be configured to operate at suitable power levels through control system 302 to provide a desired level of frequency dependent acoustic absorption. In accordance with an exemplary embodiment of the present invention, transducer 304 can comprise a transduction element having a piezoelectrically active layer, matching layers and/or other materials for generating radiation or acoustical energy that can be coupled to region of interest 306 in various manners.

Figure 4A:
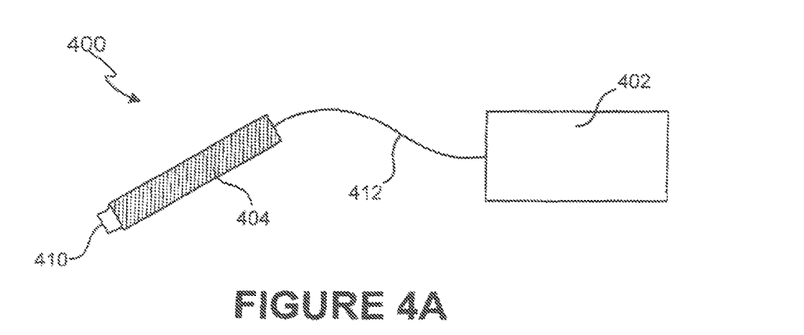
FIGS. 4A-4C illustrates a diagram of an ultra-high frequency ultrasound transducer system in accordance with an exemplary embodiment of the present invention.
Figure 4B:
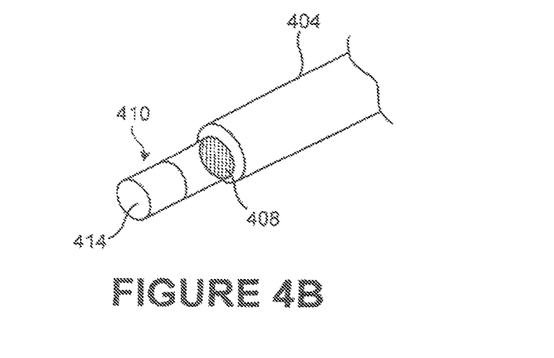
Figure 4C:
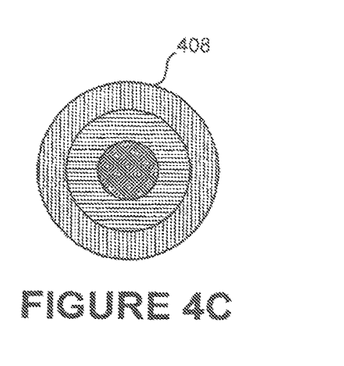

For example, with reference to FIGS. 4A-4C, in accordance with an exemplary embodiment of the present invention, an exemplary ultra-high frequency ultrasound system 400 comprises a control system 402 and a transducer 404. Control system 402 can comprise various circuit configurations for control of transducer 404, e.g., to provide drive signals to transducer 404. Control system 402 can also be coupled to transducer 404 in various manners, such as through a direct electrical connection through a cable 412, and/or through other coupling mechanisms, including capacitive coupling, thermo-acoustic coupling, and/or broadband, narrowband or high-pass acoustic filtering. Control system 402 can also he coupled to transducer 404 by inducing RF fields to transducer 404. For example, a periodic electric field can be polarized along the fully excited length of a transduction element within transducer 404, such as along the x-axis of a X-cut rod of crystalline quartz or other crystal or piezoelectric element or polarized ferroelectrics material.

In accordance with an exemplary embodiment, transducer 404 comprises a housing 406, a transduction element 408 and an application device 410. Housing 406 is suitably configured to enclose or encapsulate components of transducer 404. Housing 406 can comprise any conventional housing or enclosure suitably for containing transducer elements and components, and can be shaped and sized m various manners. For example, in accordance with an exemplary embodiment, housing 406 can be configured in the shape of a pen or stylus. However, housing 406 can be configured in any manner to allow for maneuvering and positioning of application device 410 along the skin surface of a patient.

Transduction element 408 can comprise a piezoelectrically active material, or any piezoelectric or polarized ferroelectric material crystal, ceramic, plastic, and/or like composite materials. For example, transduction element 408 can compose lead zirconante titanate (PZT), or any other piezoelectrically active material. Transduction element 408 can also comprise piezoelectric crystals, such as lithium niobate (LiNbO$_3$), lead titanate, barium titanate, quartz (SiO$_2$) and/or lead metaniobate, any polarized ferroelectric material, or any other crystals that possess low to very low dielectric and mechanical losses. Such elements and crystals can be suitably cut or shaped in various manners, such as Y-cut and X-cut configurations, e.g., an approximate 36-degree Y-cut lithium niobate crystal and an X-cut quartz crystal can exhibit excellent characteristics.

In addition to or instead of a piezoelectrically active material or crystals, transducer 404 may comprise any other materials configured for generating radiation and/or acoustical energy. Transducer 404 may also comprise one or more matching layers configured along with transduction element 408, e.g., coupled to the piezoelectrically active material, to optimise the acoustic output. For example, using matching layers designed for the fundamental resonant frequency of transduction element 408 can also cause matching of transduction element 408 at odd harmonic resonant frequencies as well. Any such matching layers can comprise thin films at higher frequencies, as opposed to thicker films used with low-frequency transducers that can vastly require an increase in acoustic power requirements.

The thickness of transduction element 408 of transducer 404 may be selected to provide a nominal or center operating frequency of a moderately high range, such as from approximately 10 MHz to 30 MHz or more, to facilitate greater resolution. For example, an approximately 4 mm diameter crystal, such as lithium niobate, having a 25 MHz nominal frequency can provide excellent efficiency, e.g., low dielectric losses, when operating at ultra-high frequencies, including within the range from approximately 20 MHz to 400 MHz or more. In addition, various crystalline materials can be suitably lapped in thickness to a high precision such that overtones, e.g., approximately odd harmonics, can be driven with high efficiency. Selecting the thickness of transduction element 408 and the resulting nominal frequency for operation can be based on the degree and balance of energy penetration and resolution that is desired for a treatment application.

Transduction element 408 can comprise a single transduction element for generating acoustical energy. Transduction element 408 can also comprise multiple elements, such as that illustrated in FIG. 4C. For example, transduction element 408 can be suitably diced in a plurality of sections that can be suitably configured to focus on the treatment region at a certain depth and/or spot size within the region of interest. Transduction element 408 can be configured as multiple elements in various arrangements, such as that set forth in U.S. application Ser. No. 11/163,148, filed Oct. 6, 2005, entitled "Method and System for Controlled Thermal Injury" published as US 2006-0116671 on Jun. 1, 2006, and hereby incorporated by reference. In addition, a multiple element configuration for transduction element 408 can also be configured with electronic focusing to provide spot-size control. Electronic focusing can be implemented in various manners, such as that set forth in U.S. application Ser. No. 10/944,500, filed Sep. 10, 2004, entitled "System and Method for Variable Depth Ultrasound" published as US 2006-0053664 on Mar. 16, 2006, and hereby incorporated by reference.

Application device 410 is configured to facilitate coupling of the acoustical energy to a region of interest, such as to the superficial and/or internal superficial regions. In accordance with an exemplary embodiment, application device 410 can comprise a standoff, a waveguide, or any other isolation/protection layer configured to enable transducer 404 to provide acoustical energy to the patient. Application device 410 can also comprise various sixes, shapes and configurations. For example, application device 410 can comprise a transparent, solid standoff such that a physician can precisely contact any small lesions in the epidermis region of the patient, and allow transducer 404 and application device 410 to be suitably sterilised for further use. In addition, application device 410 can comprise a non-transparent disposable applicator tip, and/or an applicator tip that can be suitably replaced for different patients. Applicator device 410 can also be configured in various lengths, for example as a long waveguide of several millimeters, or as a shorter applicator tip of approximately 1 mm to a few hundred micrometers in length. Shorter lengths can allow for more efficient acoustic output as compared to longer lengths for a waveguide that can alter the frequency response of the transduction element 408/applicator device 410. In any event, the selection of length can be based upon the desired operating characteristics.

Applicator device 410 may be configured in various manners for coupling to the patient to provide treatment to the superficial and/or internal superficial regions of interest. For example, applicator device 410 can comprise materials and composites having very low acoustical losses, such as fused silica, or any other low loss materials. In addition, a tip 414 of applicator device 410 can comprise a substantially flat shape for coupling to the outer skin layer of a patient, a concave-like depression configured to focus acoustic energy to the region of interest, and/or an optical magnifier configured to visually magnify the outer skin layer of the patient as applicator device 410 is being coupled. Applicator device 410 can also be suitably coupled through a thin film of a low-loss coupling fluid, such as water or other commonly used coupling fluids for use with ultrasound transducers.

As discuss above, control system 402 can be configured in various manners for control of transducer 404. For example, control system 402 can comprise a processor, a display, and/or one or more input devices. Control system 402 can also comprise other devices and components, such power supplies, amplifiers, and/or filler devices. Such devices and components can be configured within a suitably electronic controls cabinet, housing or other enclosure. In accordance with an exemplary embodiment of the present invention, control system 402 comprises a drive circuit configured to control the operation of an exemplary ultra-high frequency ultrasound transducer.

An exemplary drive circuit can be configured in various manners. For example, with reference to FIG. 5A, a drive circuit 500 can comprise a driver 502 and a feedback network 504 configured in an oscillator-based, closed-loop arrangement to drive the frequency of transducer 404 in a controlled manner for maximum efficiency. In accordance with an exemplary embodiment, drive circuit 500 is configured to drive the frequency of the transduction element at the resonant frequency to facilitate maximum efficiency.

Figure 5A:
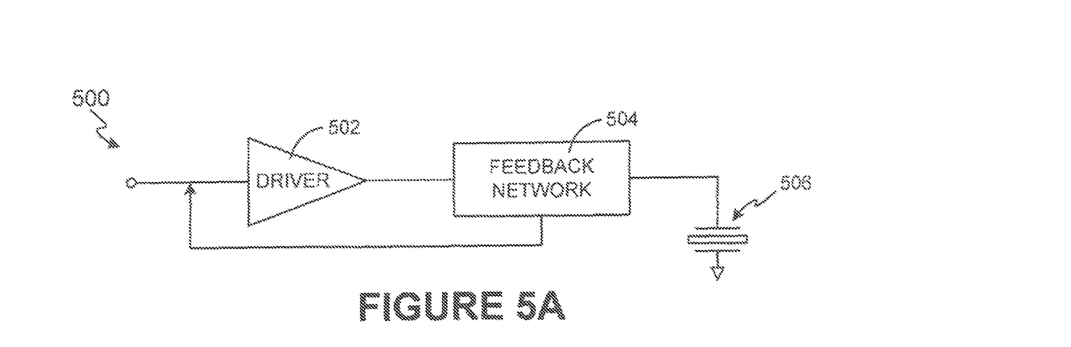
FIGS. 5A and 5B illustrate exemplary embodiments for control systems in accordance with the present invention.

Driver 502 is configured to control power to a transduction element 506, e.g., a crystal or other suitable transduction element. Driver 502 can comprise various configurations. For example, driver 502 can comprise a power/oscillator driver, a linear power amplifier, or any other power source for providing power to drive a transduction element to create acoustical energy.

Feedback network 504 is configured to use electrical signals from driver circuit 502 and/or transduction element 506 to facilitate control of the frequency of operation, and thus provide optimum electro-acoustic conversion of energy. To maintain high electro-acoustical energy conversion efficiency, feedback network 504 can suitably facilitate control of the drive frequency to within a small fraction of the resonance frequency of transduction element 506.

Feedback network 504 comprises a closed-loop circuit, e.g., a self oscillating or resonant circuit, to maintain the operating frequency of transduction element 506 in a manner that can enable optimum electro-acoustic conversion of energy. In other words, feedback network 504 is configured to cause driver circuit 502 to oscillate at the resonant frequency of frequency of transduction element 506, such as the frequency of crystal resonance. Feedback network 504 can create a 360-degree phase shift in the feedback loop of drive circuit 500. In addition, the configuration of feedback element 504 can provide a loop gain greater than or equal to one (1), thereby causing oscillation.

Figure 5B:
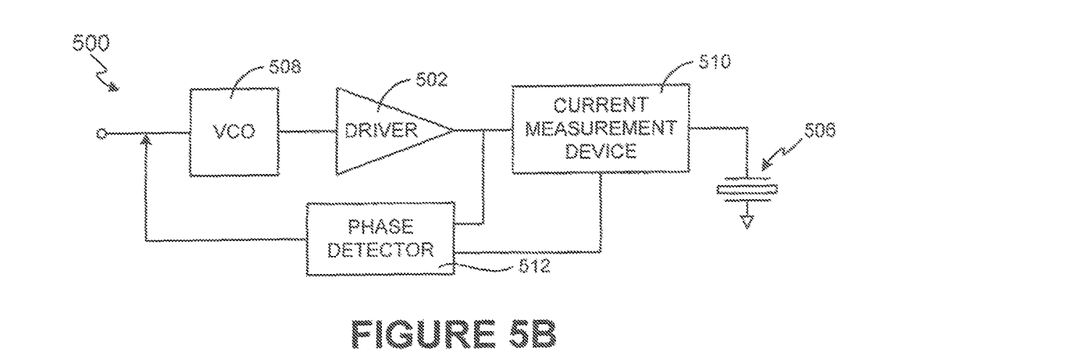

In addition to an oscillator-teed drive circuit as illustrated in FIG. 5A, in accordance with another exemplary embodiment, with reference to FIG. 5B, drive circuit 500 can also comprise a voltage-controlled oscillator (VCO) based drive circuit. For example, drive circuit 500 can be configured with a power oscillator driver comprising driver 502 and a voltage-controlled oscillator (VCO) 508 and a feedback network comprising a current measurement device 510 and a phase detector 512. VCO 508 has an output signal coupled to the input of driver 502. VCO 508 can comprise any voltage-controlled oscillator circuit or device that can be configured to the nominal resonance frequency of the transduction element, e.g., the nominal resonance frequency of crystal 506. Current measurement device 510 can comprise one or more devices or components configured for measurement of the drive current from driver 502. For example, current measurement device 510 can comprise various current sensors, amplifiers or other measurement devices. Phase detector 512 is configured to receive voltage and current signals from driver 502 and current measurement device 510 and to provide a control signal to VCO 508. For example, since VCO 508 is configured to the resonance frequency of crystal 506, the current and voltage are in phase for crystal 506 since crystal tends to he resistive at the resonance frequency. However, when crystal 506 departs from the resonant frequency, the electrical impedance of crystal 506 becomes capacitive, and the current and voltage move out of phase. Thus, phase detector 512 can suitably measure the phases of the voltage and current and determine the phase differences to generate a correction voltage that can fine-tune the frequency of VCO 508 to the optimal frequency of oscillation.

Whether configured as an oscillator-based or VCO based drive circuit, or any other drive circuit configuration, drive circuit 500 can provide for high efficiency through electronic tuning, e.g., tracking of the optimal efficiency point, through use of a feedback network configured to facilitate control of the drive frequency to within a small fraction of the resonance frequency of transduction element 506. Since fits resonant frequency of transduction elements can change due to loading, e.g., when application device 410 acoustically interlaces with the outer skin layers, drive circuit 500 can suitably control the drive frequency to thus maintain the optimum operating efficiency for a selected ultra-high frequency range of operation.

In addition, drive circuit 500 can be configured for driving transduction element 506 with either continuous waves of energy or short pulses of energy. Use of short pulses of energy can allow for an increase in the acoustic intensity level versus continuous waves of energy; however, drive circuit 500 is configured to make the acoustic intensity very large at the outer skin layers, e.g., the epidermis layer, and then have the acoustic intensity drop rapidly to lower levels, thus enabling continuous wave energy to also be used without detrimental effects to regions below the treatment regions of the patient. Moreover, by operating at optimum efficiency, the acoustic intensity can be suitably configured at high levels with use of moderate power output levels, e.g., a steady-state ultrasound intensity of approximately between 80 mW/cm$^2$ and 100 mW/cm$^2$ can cause sufficient but safe heating of the outer skin layer to facilitate treatment In accordance with another aspect of the present invention, an exemplary ultra-high-frequency ultrasound transducer system can be configured for providing ultrasound treatment to various regions within the superficial and/or internal superficial regions of the patient. For example, the region of treatment can be suitably moved below the superficial region through control of the frequency of the transduction element by suitably decreasing the frequency from ultra-high frequency levels, e.g. 300 MHz or more, to extremely high frequency levels, e.g., 100 MHz.

In addition, the region of treatment can also be suitably moved below the superficial region through the cooling of the exemplary application device for the transducer. For example, with reference again to FIG. 4B, through controlled cooling of applicator tip 414, conductive cooling can occur at the outer skin surface, e.g., proximate the point of contact of application device 410 and the outer skin layer. Accordingly, applicator tip 414 and the outer skin surface can come into thermal equilibrium, thus sparing the outer skin layer from heating effects that are effectively "pushed" below the superficial region. Such controlled cooling can be utilized with and without additional frequency control to move the treatment region below the superficial region.

In accordance with an exemplary embodiment, closed-loop temperature control can be suitably utilized to actively control the temperature of applicator tip 414. For example, the cooling can be achieved through circulating water through a water-circulating member configured proximate to or within application tip 414, such as a thin non-absorbing membrane that can retain water and allow circulation. In accordance with other exemplary embodiments, the application device 410 can be configured with electrical-based cooling control to suitably control the temperature of applicator tip 414, such as through the use of thermoelectric modules, heat sinks, and/or temperature sensors and the like configured proximate to or within application tip 414. As a result of controlled cooling of the temperature of application device 410 and/or the controlling of frequency, the region of treatment can he suitably moved below the superficial region.

In accordance with another aspect of the present invention, an exemplary ultra-high frequency transducer system may be configured to enable energy deposition at not only a fundamental frequency of transduction element 408 of transducer 404, but also at corresponding subharmonic frequencies of the piezoelectric or other acoustically-active material as well. Energy is provided to a treatment region at its peak when a piezoelectrically active material is driven at its fundamental frequency. Different piezoelectric and/or other acoustically-active materials have different fundamental frequencies. In accordance with an exemplary embodiment, energy can also be deposited at smaller peaks, i.e., at subharmonic frequencies, when the piezoelectric material is driven at its fundamental frequency. The use of the subharmonic characteristics of transducer 404 may he controlled and enabled through various focusing techniques.

Figure 6:
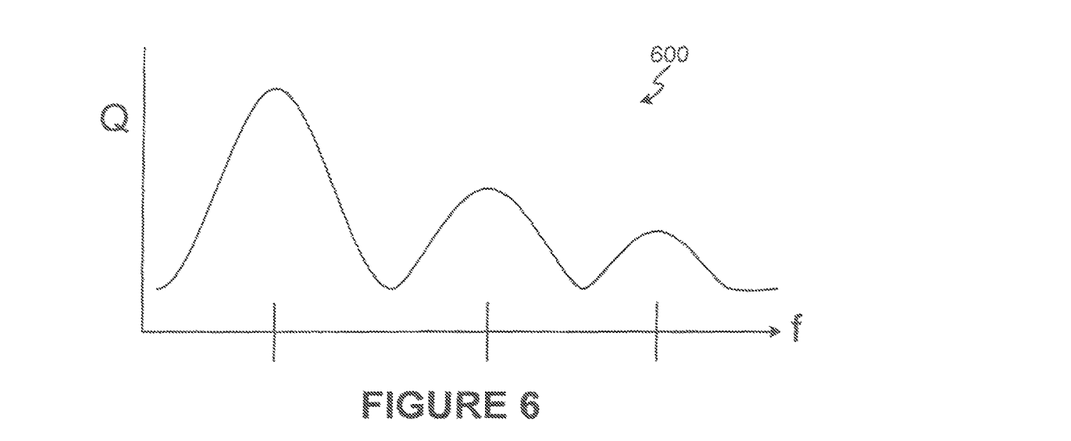
FIG. 6 illustrates an exemplary diagram of treatment characteristics of an exemplary transducer operating at the fundamental frequency and subharmonies in accordance with the present invention.

In accordance with an exemplary embodiment, enablement of the harmonics allows for treatment at various depths corresponding to the different harmonies. For example, with additional reference to frequency-harmonics curve illustrated in FIG. 6, ultra-high frequency transducer system 400 may treat various regions within the superficial and/or internal superficial regions of the patient, as represented by curve 600. Driving harmonic frequencies through transducer 404 enables treatment of a first superficial region, treatment of a second shallower region just below the former region, etc.

The present invention has been described above with reference to various exemplary embodiments. However, those skilled in the art will recognize that changes and modifications may be made to the exemplary embodiments without departing from the scope of the present invention. For example, the various operational steps, as well as the components for carrying out the operational steps, may be implemented in alternate ways depending upon the particular application or in consideration of any number of cost functions associated with the operation of the system, e.g., various of the steps may be deleted, modified, or combined with other steps. Further, it should be noted that while the method and system for ultra-high frequency ultrasound treatment with a transducer is described above is suitable for use by a medical practitioner proximate the patient, the control system can also be accessed remotely, i.e., the medical practitioner can view and/or operate the control system through a remote display or other remote I/O devices having imaging information transmitted in various manners of communication, such as by satellite/wireless or by wired connections such as IP or digital cable networks and the like, and can direct a local practitioner as to the suitably placement for the transducer. These and other changes or modifications are intended to be included within the scope of the present invention, as set forth in the following claims.

The invention claimed is:

1. A method for providing treatment to a patient, the method comprising:
    coupling an ultrasound transducer to a skin surface of a patient;
    emitting energy from the ultrasound transducer in a frequency range from about 10 MHz to about 30 MHz or in a frequency range from about 20 MHz to about 500 MHz into a superficial region of interest below the skin surface of the patient, the superficial region of interest consisting of a subcutaneous layer of skin, thereby ablating tissue in a portion of the region of interest, thereby creating a lesion in the tissue at a depth of a range of 0.1 µm to 100 µm below the skin surface; and
    sparing tissue at the depth of greater than 100 µm below the skin surface from damage from the ablating tissue.

2. The method according to claim 1, wherein the subcutaneous layer of skin comprises an epidermis layer.

3. The method according to claim 1, further comprising imaging at least a portion of the superficial region of interest; and
    displaying the at least a portion of the superficial region of interest.

4. The method according to claim 1, wherein the emitting energy from the ultrasound transducer is in a power range of 80 W/cm$^2$ to 100 W/cm$^2$.

5. The method according to claim 1, wherein the emitting energy from the ultrasound transducer is in a power range of 15 W/cm$^2$ to 500 W/cm$^2$.

6. The method according to claim 5, wherein the emitting energy from the ultrasound transducer is in a power range of about 500 W/cm$^2$ at a depth of about 0.1 µm below the skin surface.

7. The method according to claim 5, wherein the emitting energy from the ultrasound transducer is in a power range of about 15 W/cm$^2$ at a depth of about 100 µm below the skin surface.

8. The method according to claim 1, wherein the emitting energy from the ultrasound transducer is in a frequency range from about 20 MHz to about 500 MHz.

9. The method according to claim 1, wherein the emitting energy from the ultrasound transducer is in a frequency range from about 10 MHz to about 30 MHz.

10. A method for treating a melanoma in a region of interest in a patient's skin, the method comprising:
- coupling an ultrasound transducer to a skin surface of the patient;
- emitting energy from the ultrasound transducer within a frequency range from about 10 MHz to about 30 MHz into the region of interest, the region of interest comprising superficial tissue at a depth in a range of 0.1 μm to 100 μm below the skin surface, thereby ablating superficial tissue in a portion of the region of interest, thereby creating a lesion in the superficial tissue, thereby treating the melanoma in the region of interest; and
- leaving tissue below the region of interest unaffected.

11. The method according to claim 10, further comprising
- imaging at least a portion of the melanoma in the region of interest; and
- displaying an image of the portion of the melanoma.

12. The method according to claim 10, wherein the emitting energy from the ultrasound transducer is in a power range of 80 W/cm$^2$ to 100 W/cm$^2$.

13. The method according to claim 10, wherein the emitting energy from the ultrasound transducer is in a power range of 15 W/cm$^2$ to 500 W/cm$^2$.

14. The method according to claim 13, wherein the emitting energy from the ultrasound transducer is in a power range of about 500 W/cm$^2$ at a depth of about 0.1 μm below the skin surface.

15. The method according to claim 13, wherein the emitting energy from the ultrasound transducer is in a power range of about 15 W/cm$^2$ at a depth of about 100 μm below the skin surface.

16. A method for providing ultrasound treatment to a patient, the method comprising:
- operating a transducer to emit acoustical energy within a frequency range from about 10 MHz to about 30 MHz or from about 20 MHz to about 500 MHz;
- coupling the transducer to a region of interest consisting of a superficial region and a subcutaneous region;
- focusing a first acoustical energy to a first depth in the region of interest, thereby ablating a portion of superficial tissue in the superficial region, thereby creating a first lesion in the superficial tissue;
- focusing a second acoustical energy to a second depth in the region of interest, thereby ablating a portion of subcutaneous tissue in the subcutaneous region, thereby creating a second lesion in the subcutaneous tissue; and
- leaving tissue below the region of interest unaffected.

17. The method according to claim 16, wherein the superficial region is at a depth in a range of 0.1 μm to 100 μm below a skin surface and the subcutaneous region is at a depth in a range of 100 μm to 3 mm below the skin surface.

18. The method according to claim 16, wherein the first acoustical energy and the second acoustical energy is within the frequency range from about 10 MHz to about 30 MHz.

19. The method according to claim 16, wherein the first acoustical energy and the second acoustical energy is in a power range of 15 W/cm$^2$ to 500 W/cm$^2$.

20. The method according to claim 16, further comprising treating a melanoma in at least a portion of the region of interest.

* * * * *